United States Patent
Lee et al.

(10) Patent No.: US 11,982,940 B2
(45) Date of Patent: *May 14, 2024

(54) PHOTOACID GENERATOR, PHOTORESIST COMPOSITION INCLUDING THE SAME, AND METHOD OF PREPARING THE PHOTOACID GENERATOR

(71) Applicant: Samsung Electronics Co., Ltd., Suwon-si (KR)

(72) Inventors: Eunkyung Lee, Seoul (KR); Sumin Kim, Suwon-si (KR); Hyunwoo Kim, Seongnam-si (KR); Juhyeon Park, Hwaseong-si (KR); Giyoung Song, Asan-si (KR); Sukkoo Hong, Suwon-si (KR); Yoonhyun Kwak, Seoul (KR); Youngmin Nam, Seoul (KR); Byunghee Sohn, Yongin-si (KR); Sunyoung Lee, Seoul (KR); Aram Jeon, Seoul (KR); Sungwon Choi, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/313,555

(22) Filed: May 8, 2023

(65) Prior Publication Data
US 2023/0324791 A1    Oct. 12, 2023

Related U.S. Application Data

(63) Continuation of application No. 17/238,355, filed on Apr. 23, 2021, now Pat. No. 11,693,315.

(30) Foreign Application Priority Data

Nov. 27, 2020 (KR) .................. 10-2020-0163340

(51) Int. Cl.
    G03F 7/004    (2006.01)
    C07C 309/12   (2006.01)
    (Continued)

(52) U.S. Cl.
    CPC .......... *G03F 7/0045* (2013.01); *C07C 309/12* (2013.01); *C07C 381/12* (2013.01);
    (Continued)

(58) Field of Classification Search
    None
    See application file for complete search history.

(56) References Cited

U.S. PATENT DOCUMENTS 10,802,399 B2   10/2020   Nishio et al.
11,009,790 B2    5/2021   Hong et al.
(Continued)

FOREIGN PATENT DOCUMENTS

EP    0972761 A      1/2000
JP    2015054833 A   3/2015
(Continued)

OTHER PUBLICATIONS

English Abstract of JP 2018-118962.
(Continued)

*Primary Examiner* — Sean M DeGuire
*Assistant Examiner* — Andrew Preston Traywick
(74) *Attorney, Agent, or Firm* — CANTOR COLBURN LLP

(57) ABSTRACT

Disclosed are a photoacid generator, a photoresist composition including the same, and a method of preparing the photoacid generator. The photoacid generator may include a compound represented by Formula 1:

(Continued)

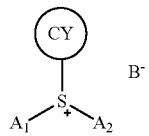

Formula 1 wherein, in Formula 1, CY, A1, A2, and B are respectively described in the specification.

21 Claims, 2 Drawing Sheets

(51) Int. Cl.
 *C07C 381/12* (2006.01)
 *C07D 333/76* (2006.01)
 *G03F 7/038* (2006.01)
 *G03F 7/039* (2006.01)
(52) U.S. Cl.
 CPC ........... *C07D 333/76* (2013.01); *G03F 7/038* (2013.01); *G03F 7/039* (2013.01); *C07C 2603/74* (2017.05)

(56) References Cited

U.S. PATENT DOCUMENTS

| | | | |
|---|---|---|---|
| 2015/0086926 | A1 | 3/2015 | Ohashi et al. |
| 2017/0369616 | A1 | 12/2017 | Hatakeyama et al. |
| 2018/0267402 | A1* | 9/2018 | Hatakeyama ......... C08F 228/02 |
| 2018/0364571 | A1* | 12/2018 | Nishio .................... G03F 7/039 |
| 2019/0094690 | A1 | 3/2019 | Hatakeyama et al. |
| 2020/0089111 | A1 | 3/2020 | Hatakeyama et al. |
| 2020/0192222 | A1 | 6/2020 | Hatakeyama et al. |

FOREIGN PATENT DOCUMENTS

| | | |
|---|---|---|
| JP | 2018118962 A | 8/2018 |
| JP | 2020015713 A | 1/2020 |
| JP | 2020059708 A | 4/2020 |
| JP | 2020083878 A | 6/2020 |
| JP | 2020098330 A | 6/2020 |
| KR | 1020180013781 A | 2/2018 |
| KR | 1020180100186 A | 9/2018 |
| KR | 1020200032644 A | 3/2020 |

OTHER PUBLICATIONS

English Abstract of JP 2020-015713.
English Abstract of JP 2020-059708.
English Abstract of JP 2020-083878.
Siu etal., RSCAdv., 2017, 7, 7623, Thermally robust triarylsulfonium ionic liquids stable in air for 90 days at 300 C (year 2017).

* cited by examiner

PHOTOACID GENERATOR, PHOTORESIST COMPOSITION INCLUDING THE SAME, AND METHOD OF PREPARING THE PHOTOACID GENERATOR

CROSS-REFERENCE TO RELATED APPLICATION

This is a continuation application of U.S. application Ser. No. 17/238,355 filed Apr. 23, 2021, now U.S. Pat. No. 11,691,315, which in turn claims priority to Korean Patent Application No. 10-2020-0163340, filed on Nov. 27, 2020, in the Korean Intellectual Property Office, and all the benefits accruing therefrom under 35 U.S.C. §§ 119, 120, the entire contents of which are incorporated by reference herein.

BACKGROUND

1. Field

The present disclosure relates to photoacid generators, photoresist compositions including the same, and methods of preparing the photoacid generators.

2. Description of the Related Art

In manufacturing a highly integrated semiconductor device, pattern miniaturization is essential. Recently, as designs of semiconductor devices rapidly decrease in size, various lithography techniques for implementing fine patterns have been developed. In particular, an extreme ultraviolet (EUV) lithography technique using an exposure process by EUV with a wavelength of about 13.5 nanometers (nm) is a next-generation technique to replace a lithography process using a KrF excimer laser (248 nm) and an ArF excimer laser (193 nm), and various studies on EUV lithography techniques are being conducted.

An EUV lithography process has a different mechanism of action from a lithography process using a KrF excimer laser and an ArF excimer laser. In an EUV lithography process, the entire process is carried out under vacuum. In EUV lithography equipment, power required to irradiate a laser from a light source is insufficient, so there is a limitation in increasing the dose sufficiently to generate a required amount of acid from a photoacid generator in a photoresist material during exposure.

However, when performing the EUV lithography process using a photoresist material containing a conventional photoacid generator, due to the low dose provided from the light source of the EUV lithography equipment, acid generation efficiency is low, and exposure speed is low, thereby making it difficult to obtain desired exposure sensitivity and resolution.

Accordingly, there is still demand for a novel photoacid generator having excellent lithography characteristics such as exposure sensitivity and resolution and an excellent pattern shape, a photoresist composition including the same, and a method of preparing the photoacid generator.

SUMMARY

Provided are novel photoacid generators having improved lithography characteristics such as exposure sensitivity and resolution and an improved pattern shape.

Provided are photoresist compositions including the photoacid generators.

Provided are methods of preparing photoacid generators having high purity.

Additional aspects will be set forth in part in the description which follows and, in part, will be apparent from the description, or may be learned by practice of the presented embodiments of the disclosure.

According to an aspect of an embodiment,
a photoacid generator includes a compound represented by Formula 1:

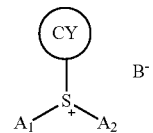

Formula 1 wherein, in Formula 1,
CY is an unsubstituted C6-C10 aromatic ring group, or a C6-C10 aromatic ring group substituted with a halogen atom, a C1-C30 alkyl group, or a C1-C30 haloalkyl group,
$A_1$ and $A_2$ are each independently a substituted C4-C60 aliphatic ring group, a C3-C60 heteroaliphatic ring group, a substituted C6-C60 aromatic ring group, or a substituted C5-C60 heteroaromatic ring group, or $A_1$ and $A_2$ are combined with each other together with a sulfur atom, to form a ring substituted with at least two iodine atoms, and
B is a counter anion.

According to an aspect of an embodiment,
a photoresist composition includes the aforementioned photoacid generator, a base polymer, a photodegradable quencher (PDQ), and a solvent.

According to an aspect of an embodiment,
a method of preparing a photoacid generator includes preparing a cation moiety of a photoacid generator, represented by Formula 10, through an electrophilic aromatic substitution reaction of a compound represented by Formula 9:

Formula 9 wherein, in Formula 9,
$A_3$ and $A_4$ are each independently a substituted C4-C60 aliphatic ring group, a C3-C60 heteroaliphatic ring group, a substituted C6-C60 aromatic ring group, or a substituted C5-C60 heteroaromatic ring group, or $A_3$ and $A_4$ are combined with each other together with a sulfur atom, to form a ring substituted with at least two iodine atoms,

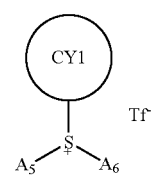

Formula 10 wherein, in Formula 10,
CY1 is an unsubstituted C6-C10 aromatic ring group, or a C6-C10 aromatic ring group substituted with a halogen atom, a C1-C30 alkyl group, or a C1-C30 haloalkyl group,
$A_5$ and $A_6$ are each independently a substituted C4-C60 aliphatic ring group, a C3-C60 heteroaliphatic ring group, a substituted C6-C60 aromatic ring group, or a substituted C5-C60 heteroaromatic ring group, or $A_5$ and $A_6$ are combined with each other together with a sulfur atom, to form a ring substituted with at least two iodine atoms, and
Tf is $(CF_2SO_2)_2O$.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
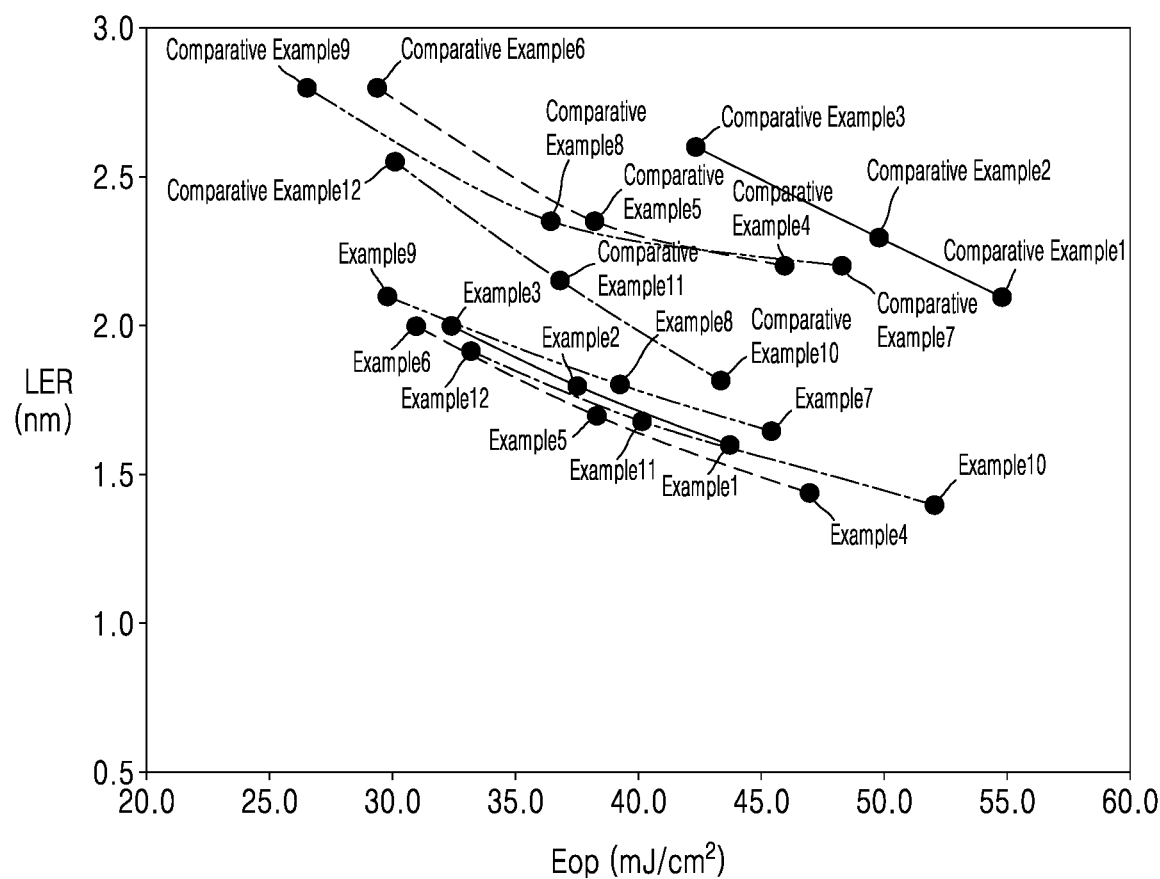
FIG. 1 is a graph illustrating Line edge roughness (LER) with respect to optimum energy ($E_{op}$) of photoresist patterns formed using photoresist compositions of Examples 1 to 12 and Comparative Examples 1 to 12.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Hereinafter, a photoacid generator according to an embodiment, a photoresist composition including the same, and a method of preparing the photoresist composition will be described in detail with reference to the attached drawings. These embodiments are presented merely to explain the present invention more specifically, and the scope of the present invention is not limited by these embodiments and is only defined by claims to be described later.

It will be understood that when an element is referred to as being "on" another element, it can be directly in contact with the other element or intervening elements may be present therebetween. In contrast, when an element is referred to as being "directly on" another element, there are no intervening elements present.

Expressions such as "at least one", "at least one kind", "one or more kinds", or "one or more" when preceding a list of elements, modify the entire list of elements and do not modify the individual elements of the list. As used herein, the term "combination thereof" is used to refer to a mixture or alloy of two or more components described above.

As used herein, the term "including" is used to indicate that other components may be added or/and interposed, rather than excluding other components, unless specifically stated to the contrary. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

As used herein, the term "first", "second", or the like do not indicate order, quantity, or importance, and are used to distinguish one element from another. It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, unless otherwise indicated or explicitly contradicted by context, it should be interpreted as including both singular and plural. For example, as used herein, the singular forms "a," "an," and "the" are intended to include the plural forms as well, unless the context clearly indicates otherwise. As used herein, the term "or" means "and/or" unless otherwise specified.

Throughout the present specification, "an embodiment", "example embodiment", "exemplary embodiment", etc. are included in at least one embodiment in which specific elements described in connection with the embodiment are included in this specification, which means that these elements may or may not exist in another embodiment. Further, it should be understood that the described elements may be combined in any suitable manner in various embodiments.

Unless otherwise defined, all terms including technical and scientific terms used herein have the same meaning as commonly understood by one of ordinary skill in the art to which this invention belongs. All cited patents, patent applications and other references are incorporated herein by reference in their entirety. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. However, if the terms in this specification contradict or conflict with the terms of the incorporated references, the terms from this specification take precedence over the conflicting terms in the incorporated reference.

While specific embodiments and implementations have been described, alternatives, modifications, variations, improvements and substantive equivalents that are currently unexpected or unforeseeable may occur to applicants or those skilled in the art. Accordingly, the appended claims and amendments are intended to include all such alternatives, modifications, improvements and substantial equivalents.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±20%, 10%, 5% of the stated value.

In any formula, * and *' each indicate a binding site to a neighboring atom or a neighboring functional group.

A photoacid generator according to an embodiment may include a compound represented by Formula 1 below:

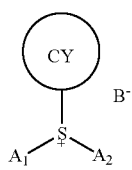

Formula 1 wherein, in Formula 1,

CY may be an unsubstituted C6-C10 aromatic ring group, or a C6-C10 aromatic ring group substituted with a halogen atom, a C1-C30 alkyl group, or a C1-C30 haloalkyl group, $A_1$ and $A_2$ may each be independently a substituted C4-C60 aliphatic ring group, a C3-C60 heteroaliphatic ring group, a substituted C6-C60 aromatic ring group, or a substituted C5-C60 heteroaromatic ring group, or $A_1$ and $A_2$ may be combined with each other together with a sulfur atom, to form a ring substituted with at least two iodine atoms, and B may be a counter anion.

In an embodiment, CY may be an unsubstituted C6-C10 aromatic ring group, a C6-C10 aromatic ring group substituted with fluorine, chlorine, or bromine, or a C6-C10 aromatic ring group substituted with a C1-C30 alkyl fluoride group, a C1-C30 alkyl chloride group, or a C1-C30 alkyl bromide group.

In an embodiment, the ring substituted with at least two iodine atoms formed by the combination of $A_1$ and $A_2$ together with a sulfur atom, may include one of rings below:

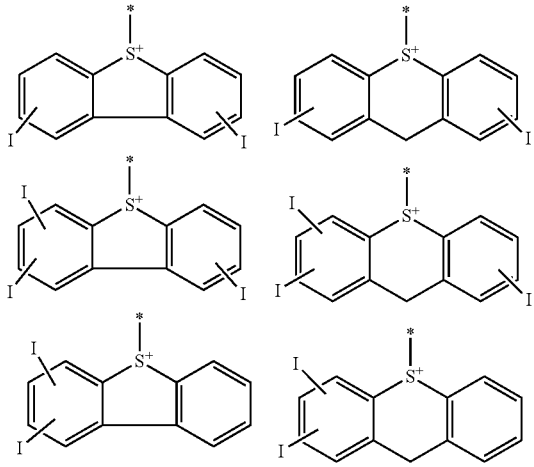

wherein * may be a binding site with the CY ring.

Since an EUV light source (13.5 nm) has a smaller number of photons compared to an ArF immersion light source, noise may increase in the boundary area between an area exposed by the EUV light source and a non-exposed area. In order to compensate for this problem, the lithography process using the EUV light source may require a large amount of photoacid generator in the photoresist composition based on the same amount of light as compared to the lithography process using other light sources. However, when the photoresist composition includes a large amount of the photoacid generator, glass transition temperature (Tg) of the base polymer may change, and thermal stability thereof may deteriorate. Further, the resolution of the formed photoresist patterns may be deteriorated due to the photoacid generator remaining during the lithography process using the EUV light source.

The photoacid generator according to an embodiment has a structure in which two or more iodine groups having a high light absorption rate are introduced as functional groups. Iodine exhibits a remarkably high light absorption rate of about $1.4 \times 10^7$ square centimeter per mole (cm$^2$/mol) or more compared to hydrogen, carbon, fluorine, chlorine, or bromine. Thus, the photoacid generator may allow the pattern formed using the EUV light source to have improved pattern resolution even with the same or less content as compared with the pattern formed using other light sources than the EUV light source.

In an embodiment, the compound may include a compound represented by Formula 2:

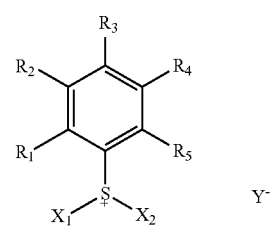

Formula 2 wherein in Formula 2, $R_1$, $R_2$, $R_3$, $R_4$, and $R_5$ may each be independently a hydrogen atom, a halogen atom, a C1-C20 alkyl group, or a C1-C20 haloalkyl group, $X_1$ and $X_2$ may each be independently a substituted C4-C50 aliphatic ring group, a C3-C50 heteroaliphatic ring group, a substituted C6-O50 aromatic ring group, a substituted C5-C50 heteroaromatic ring group, or $X_1$ and $X_2$ may be combined with each other together with a sulfur atom, to form a ring substituted with at least two iodine atoms, and Y may be a counter anion.

$R_1$, $R_2$, $R_3$, $R_4$, and $R_5$ may each be independently hydrogen, fluorine, chlorine, bromine, a C1-C20 alkyl group, a C1-C20 alkyl fluoride group, a C1-C20 alkyl chloride group, or a C1-C20 alkyl bromide group.

In an embodiment, $R_1$, $R_2$, $R_3$, $R_4$, and $R_5$ may each independently be hydrogen, fluorine, chlorine, bromine, a C1-C20 alkyl group, a C1-C20 alkyl fluoride group, a C1-C20 alkyl chloride group, or a C1-C20 alkyl bromide group.

In an embodiment, the compound may include a cation represented by Formula 3:

Formula 3

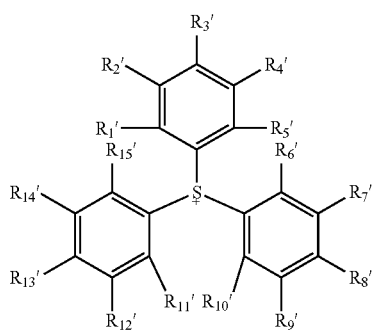

wherein in Formula 3, $R_1'$, $R_2'$, $R_3'$, $R_4'$, and $R_5'$ may each be independently a hydrogen atom, a halogen atom, a C1-C20 alkyl group, or a C1-C20 haloalkyl group, $R_6'$, $R_7'$, $R_8'$, $R_9'$, $R_{10}'$, $R_{11}'$, $R_{12}'$, $R_{13}'$, $R_{14}'$, and $R_{15}'$ may each be independently a hydrogen atom, a halogen atom, a hydroxy group, a cyano group, a substituted or unsubstituted C1-C30 alkyl group, a substituted or unsubstituted C1-C30 alkoxy group, a substituted or unsubstituted C3-C30 cycloalkyl group, a substituted or unsubstituted C6-C30 aryl group, a substituted or unsubstituted C6-C30 heteroaryl group, or $R_{10}'$ and $R_{11}'$ may be combined with each other to form a single bond, and at least two of $R_6'$, $R_7'$, $R_8'$, $R_9'$, $R_{12}'$, $R_{13}'$, $R_{14}'$, and $R_{15}'$ may be iodine atoms.

In an embodiment, $R_1'$, $R_2'$, $R_3'$, $R_4'$, and $R_5'$ may each be independently hydrogen, fluorine, chlorine, bromine, a C1-C20 alkyl group, a C1-C20 alkyl fluoride group, a C1-C20 alkyl chloride group, or a C1-C20 alkyl bromide group.

In an embodiment, the compound may include a cation represented by Formula 4 or Formula 5:

Formula 4

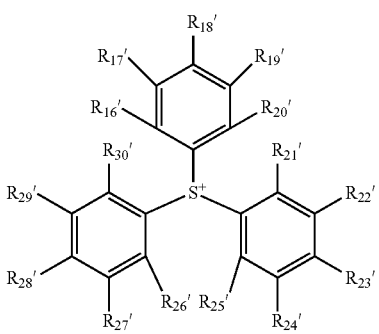

wherein in Formula 4, $R_{16}'$, $R_{17}'$, $R_{18}'$, $R_{19}'$, and $R_{20}'$ may each be independently a hydrogen atom, a halogen atom, a C1-C20 alkyl group, or a C1-C20 haloalkyl group, $R_{21}'$, $R_{22}'$, $R_{23}'$, $R_{24}'$, $R_{25}'$, $R_{26}'$, $R_{27}'$, $R_{28}'$, $R_{29}'$, and $R_{30}'$ may each be independently a hydrogen atom, a halogen atom, a hydroxy group, a substituted or unsubstituted C1-C30 alkyl group, a substituted or unsubstituted C3-C30 cycloalkyl group, a substituted or unsubstituted C6-C30 aryl group, or a combination thereof, and at least two of $R_{23}'$, $R_{24}'$, $R_{27}'$, and $R_{28}'$ may be iodine atoms, Formula 5

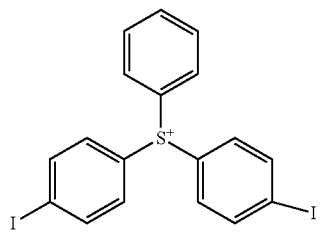

wherein in Formula 5, $R_{31}'$, $R_{32}'$, $R_{33}'$, $R_{34}'$, and $R_{35}'$ may each be independently a hydrogen atom, a halogen atom, a C1-C20 alkyl group, or a C1-C20 haloalkyl group, $R_{36}'$, $R_{37}'$, $R_{38}'$, $R_{39}'$, $R_{40}'$, $R_{41}'$, $R_{42}'$, and $R_{43}'$ may each be independently a hydrogen atom, a halogen atom, a hydroxy group, a substituted or unsubstituted C1-C30 alkyl group, a substituted or unsubstituted C3-C30 cycloalkyl group, a substituted or unsubstituted C6-C30 aryl group, or a combination thereof, and at least two of $R_{38}'$, $R_{39}'$, $R_{40}'$, and $R_{41}'$ may be iodine atoms.

In an embodiment, $R_{16}'$, $R_{17}'$, $R_{18}'$, $R_{19}'$, $R_{20}'$, $R_{31}'$, $R_{32}'$, $R_{33}'$, $R_{34}'$, and $R_{35}'$ may each be independently hydrogen, fluorine, chlorine, bromine, a C1-C20 alkyl group, a C1-C20 alkyl fluoride group, a C1-C20 alkyl chloride group, or a C1-C20 alkyl bromide group.

In example embodiments, the compound may include a cation represented by any one of 1 to 45.

1

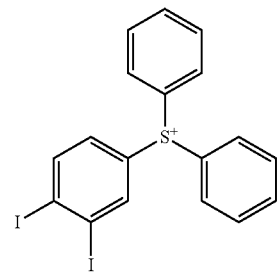

2

3
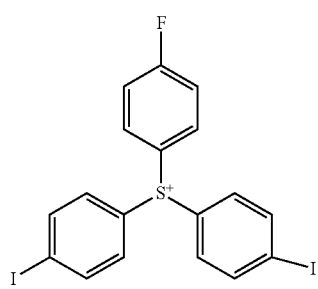
4
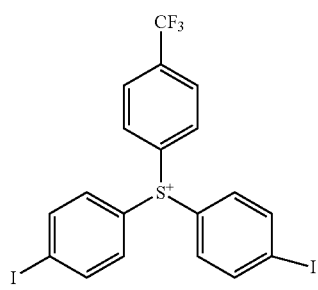
5
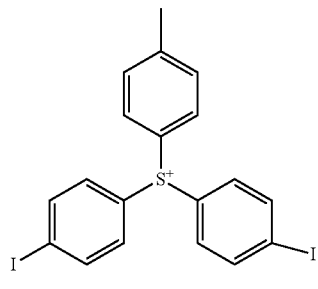
6
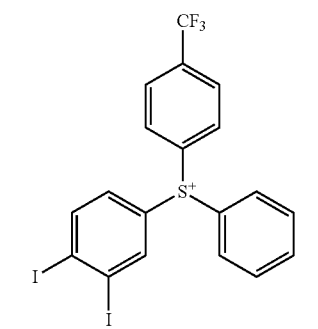
7
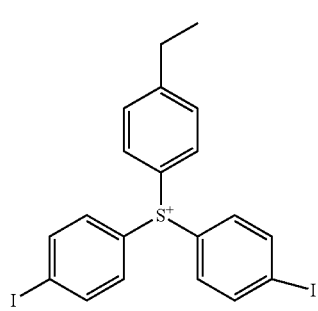
8
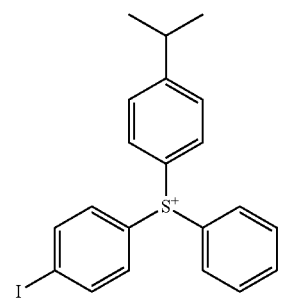
9
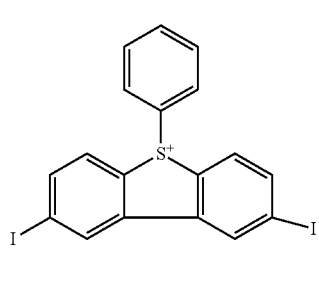
10
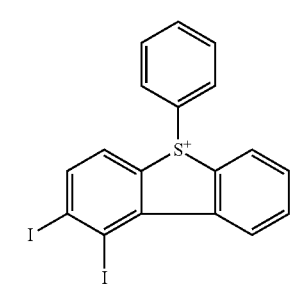
11
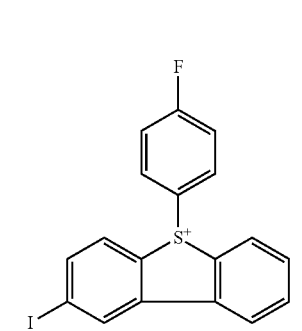
12
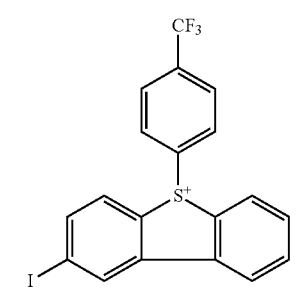

13
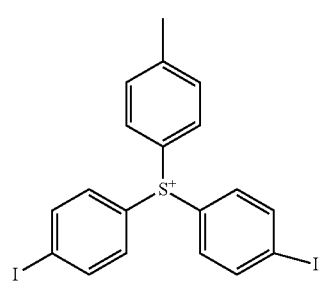
14
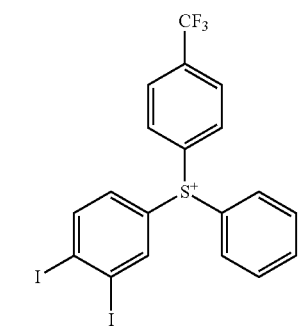
15
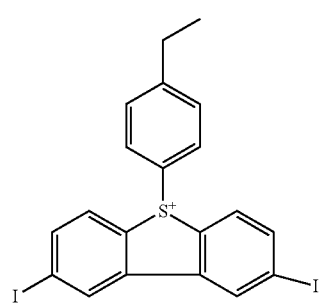
16
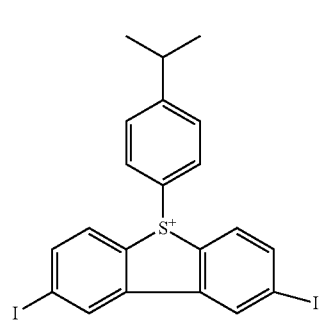
17
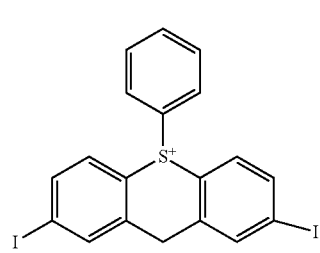
18
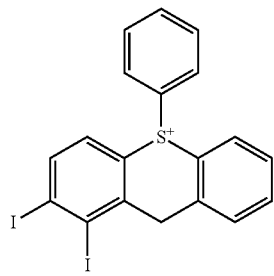
19
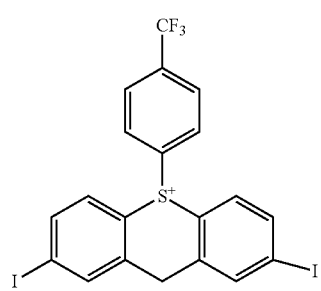
20
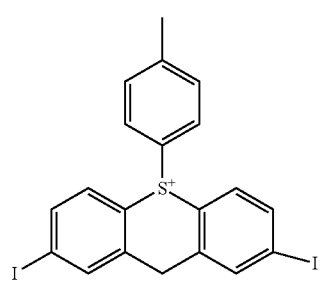
21
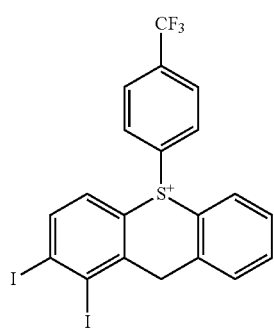
22
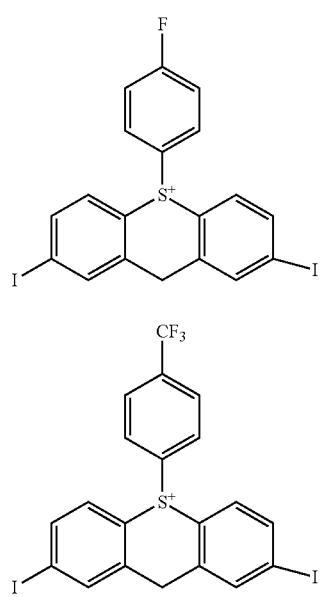

-continued
23
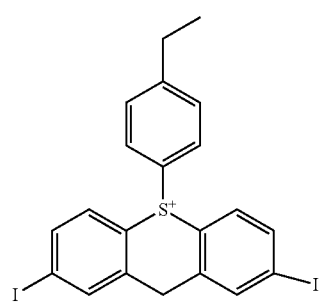
24
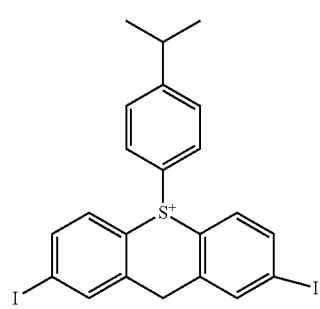
25
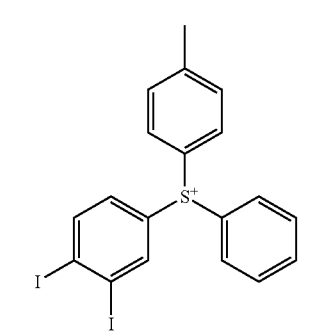
26
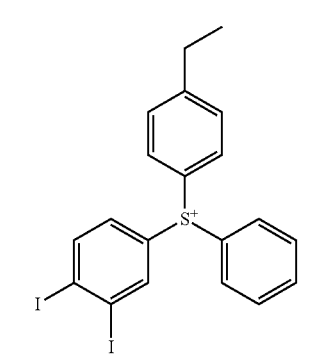
27
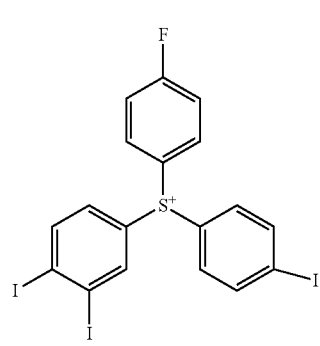
28
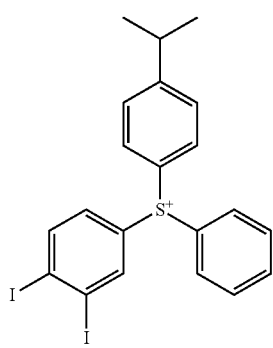
29
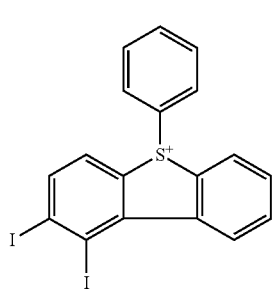
30
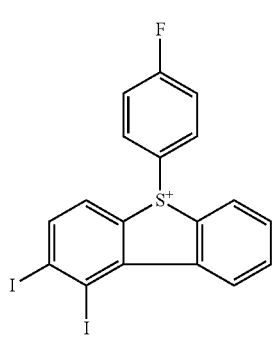
31
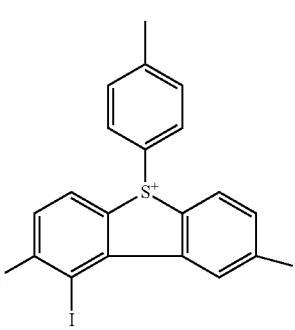
32
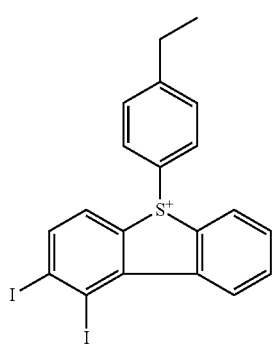

33
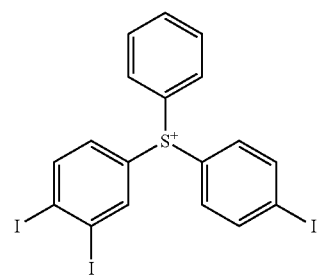
34
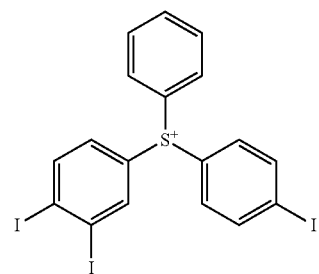
35
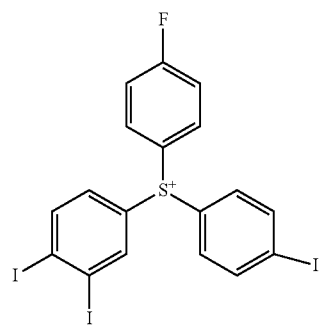
36
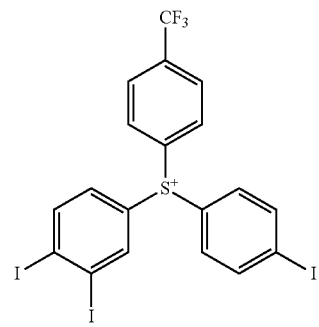
37
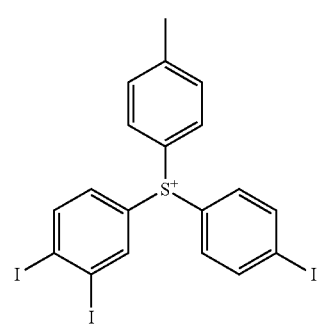
38
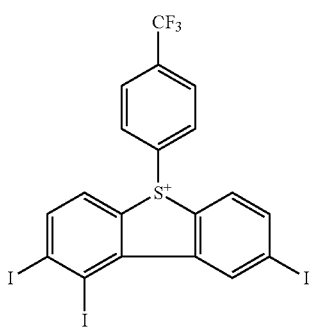
39
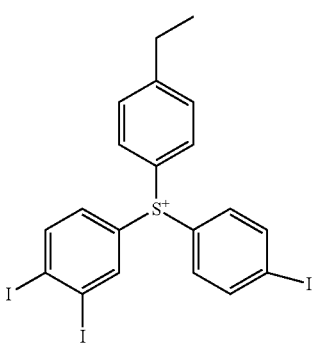
40
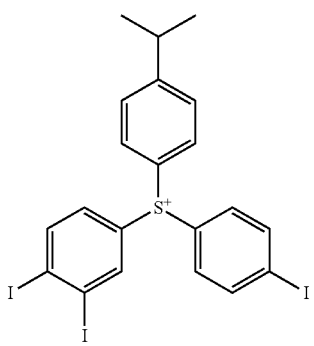
41
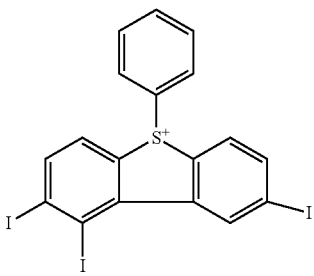
42
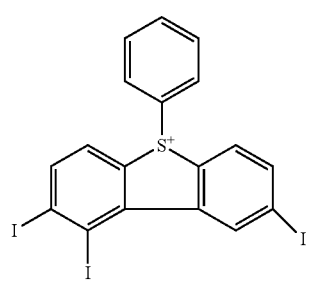

-continued

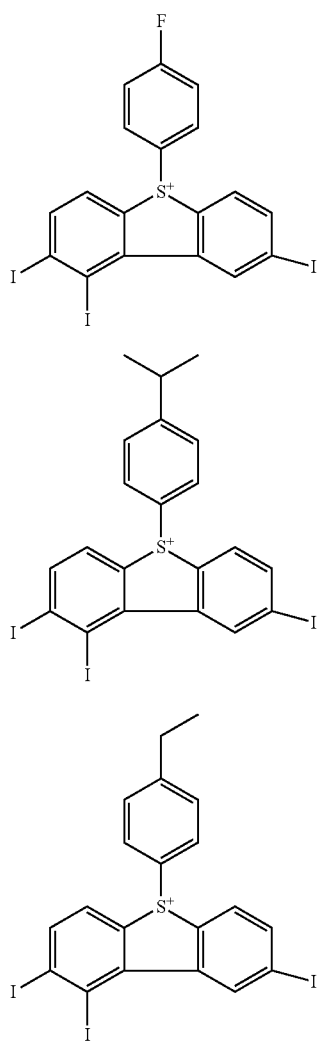

In an embodiment, the compound may include an anion represented by Formula 6:

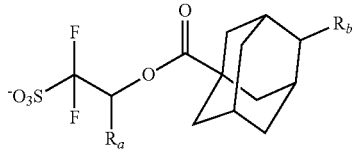

Formula 6 wherein in Formula 6, $R_a$ and $R_b$ may each be independently a hydrogen atom, a halogen atom, a C1-C20 alkyl group, or a C1-C20 haloalkyl group.

In an embodiment, $R_a$ and $R_b$ may each be independently a hydrogen atom.

A photoresist composition according to an embodiment may include: the aforementioned photoacid generator; a base polymer; a photodegradable quencher (PDQ); and a solvent.

The photoresist composition may include the photoacid generator and provide lithography characteristics such as improved exposure sensitivity and resolution, and improved pattern shape even under a small dose.

The content of the photoacid generator may be about 15 parts by weight to about 50 parts by weight based on 100 parts by weight of the base polymer. For example, about 15 parts by weight to about 45 parts by weight, about 15 parts by weight to about 40 parts by weight, about 15 parts by weight to about 35 parts by weight, about 15 parts by weight to about 30 parts by weight, about 15 parts by weight to about 25 parts by weight, and about 15 parts by weight to about 20 parts by weight based on 100 parts by weight of the base polymer. When the content of the photoacid generator is less than 15 parts by weight, the number of EUV photons is small, a light absorption rate may be lowered. When the content of the photoacid generator is more than 50 parts by weight, the T g of the base polymer may be changed, and the resolution of the formed resist patterns may be deteriorated due to the photoacid generator remaining during the lithography process using the EUV light source.

In example embodiments, the base polymer may include a polymer represented by Formula 7:

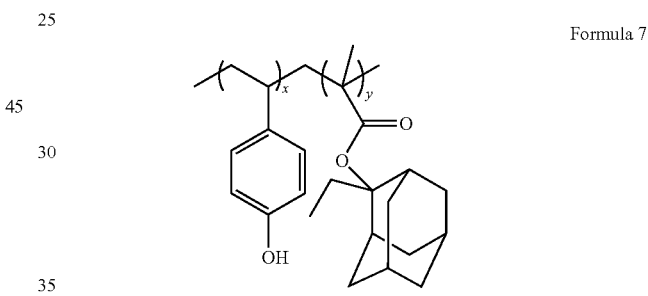

Formula 7 wherein in Formula 7, x may be an integer of 1 to 100, and y may be an integer of 1 to 100, and In an embodiment, x may be an integer of 1 to 50, and y may be an integer of 1 to 50.

The base polymer may have a structure in which a first repeating unit of hydroxystyrene and a second repeating unit having an adamantyl group as an acid-degradable protection group are copolymerized.

The content of the base polymer in the photoresist composition may be about 1 part by weight to about 25 parts by weight based on 100 parts by weight of the photoresist composition. For example, about 1 parts by weight to about 20 parts by weight, about 1 parts by weight to about 15 parts by weight, about 1 parts by weight to about 10 parts by weight, about 1 parts by weight to about 5 parts by weight, about 1 parts by weight to about 2 parts by weight, and about 5 parts by weight to about 20 parts by weight based on 100 parts by weight of the photoresist composition. When the content of the base polymer may be less than 1 part by weight, coating of the photoresist composition may not be performed easily. When the content of the base polymer may be more than 25 parts by weight, the viscosity of the photoresist composition may become too large, and thus uniform coating of the photoresist composition may be difficult.

In example embodiments, the photodegradable quencher may include a quencher represented by Formula 8:

Formula 8

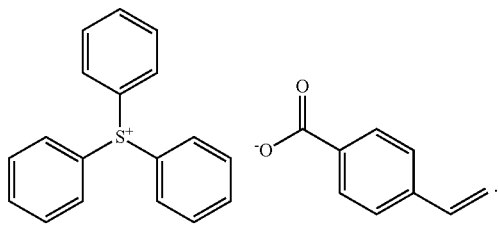

The content of the photodegradable quencher in the photoresist composition may be about 0.1 parts by weight to about 20 parts by weight based on 100 parts by weight of the base polymer, but is not limited thereto. For example, about 0.1 parts by weight to about 15 parts by weight, about 0.1 parts by weight to about 10 parts by weight, about 0.1 parts by weight to about 5 parts by weight, about 0.1 parts by weight to about 2 parts by weight, about 0.1 parts by weight to about 1 parts by weight, and about 5 parts by weight to about 10 parts by weight based on 100 parts by weight of the base polymer, but is not limited thereto.

In an embodiment, the solvent may include polypropylene glycol monomethyl ether acetate, propylene glycol monomethyl ether, or a combination thereof. However, the present invention is not limited thereto, and any suitable solvent in the art may be used.

A method of preparing a photoacid generator according to an embodiment may include: preparing a cation moiety of a photoacid generator, represented by Formula 10, through an electrophilic aromatic substitution reaction of a compound represented by Formula 9:

Formula 9

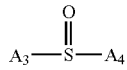

wherein in Formula 9,
$A_3$ and $A_4$ may each be independently a substituted C4-C60 aliphatic ring group, a C3-C60 heteroaliphatic ring group, a substituted C6-C60 aromatic ring group, or a substituted C5-C60 heteroaromatic ring group, or $A_3$ and $A_4$ may be combined with each other together with a sulfur atom, to form a ring substituted with at least two iodine atoms, Formula 10

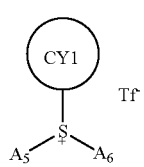

wherein in Formula 10,
CY1 may be an unsubstituted C6-C10 aromatic ring group, or a C6-C10 aromatic ring group substituted with a halogen atom, a C1-C30 alkyl group, or a C1-C30 haloalkyl group,
$A_5$ and $A_6$ may each be independently a substituted C4-C60 aliphatic ring group, a C3-C60 heteroaliphatic ring group, a substituted C6-C60 aromatic ring group, or a substituted C5-C60 heteroaromatic ring group, or $A_5$ and $A_6$ may be combined with each other together with a sulfur atom, to form a ring substituted with at least two iodine atoms, and
Tf may be $(CF_2SO_2)_2O$.

The cation moiety of the photoacid generator may be prepared by an electrophilic aromatic substitution reaction to obtain a photoacid generator having high purity. Purity of the photoacid generator is about 95% or more.

In an embodiment, the photoacid generator may include at least one of rings formed by the combination of $A_3$ and $A_4$ together with a sulfur atom substituted with at least two iodine atoms.

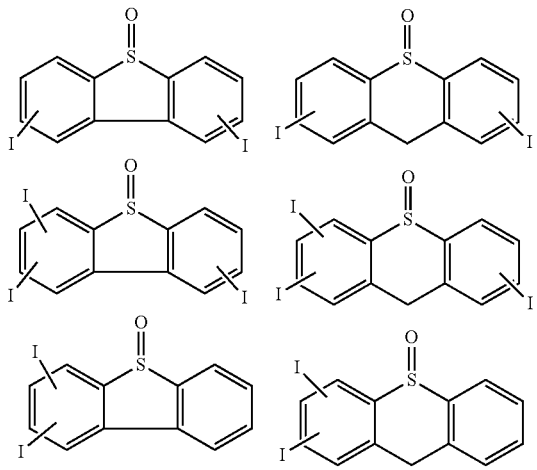

In an embodiment, the ring formed by the combination of $A_5$ and $A_6$ together with a sulfur atom substituted with at least two iodine atoms may include one of rings below:

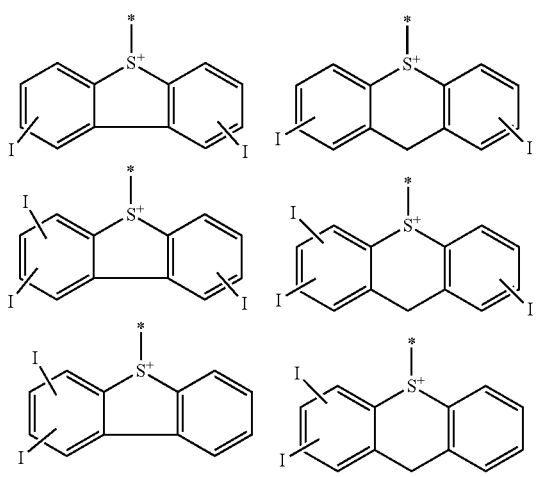

wherein * is a binding site with the CY ring.

Unless otherwise defined throughout this specification, the aliphatic ring group, heteroaliphatic ring group, aromatic ring group, and heteroaromatic ring group used in Formulas are defined as follows.

The aliphatic cyclic group may be a monocyclic or polycyclic aliphatic cyclic group. Examples of the monocyclic aliphatic ring group may include a cyclopentyl group, a cyclohexyl group, and a cyclooctyl group. Examples of the polycyclic aliphatic ring group may include a norbornyl group, a norbornenyl group, a tricyclodecanyl group, and a tetracyclodecanyl group. The heteroaliphatic ring group may be an aliphatic ring group in which at least one heteroatom N, O, P, or S is included as a ring element forming the aliphatic ring group and the remaining ring atom is C.

The aromatic ring group may be a monocyclic or polycyclic aromatic ring group. Examples of the monocyclic aromatic ring group may include a benzene ring. Examples of the polycyclic aromatic ring group may include a naphthalene ring, a phenanthrene ring, an anthracene ring, and a fluorene ring. The heteroaromatic ring group may be an aromatic cyclic group in which at least one heteroatom N, O, P, or S is included as a ring element forming the aromatic ring group and the remaining ring atom is C.

Unless otherwise defined throughout this specification, the substitution (substituent group) used in Formulas is defined as follow.

The "substitution" in the "substituted" aliphatic ring group, heteroaliphatic ring group, aromatic ring group, and heteroaromatic ring group used in the above Formulas refers to being substituted with a halogen atom, a C1-C20 alkyl group substituted with a halogen atom (for example, $CF_3$, $CHF_2$, $CH_2F$, or $CCl_3$), a hydroxy group, a nitro group, a cyano group, an amino group, an amidino group, hydrazine, hydrazone, a sulfonic acid group or a salt thereof, a phosphoric acid or a salt thereof, a C1-C20 alkyl group, a C2-C20 alkenyl group, a C2-C20 alkynyl group, a C3-C20 cycloalkyl group, a C1-C20 heterocycloalkyl group, a C6-C20 aryl group, a C6-C20 arylalkyl group, a C6-C20 heteroaryl group, or a C6-C20 heteroarylalkyl group.

An alkyl group refers to a fully saturated branched or unbranched (or straight or linear) hydrocarbon group. Non-limiting examples of the alkyl group may include methyl, ethyl, n-propyl, isopropyl, n-butyl, isobutyl, sec-butyl, n-pentyl, isopentyl, neopentyl, iso-amyl, n-hexyl, 3-methylhexyl, 2,2-dimethylpentyl, 2,3-dimethylpentyl, and n-heptyl. At least one hydrogen atom in the alkyl may be substituted with the above-described substituent.

An alkenyl group refers to an aliphatic hydrocarbon containing one or more double bonds, and an alkynyl group refers to an aliphatic hydrocarbon containing one or more triple bonds.

A cycloalkyl group refers to an aliphatic hydrocarbon containing one or more rings. In this case, the alkyl group is as described above. A heterocycloalkyl group refers to a cycloalkyl group containing one or more heteroatoms N, O, P, or S. In this case, the cycloalkyl group is as described above.

An aryl group is used alone or in combination, and refers to an aromatic hydrocarbon containing one or more rings. The aryl groups also include a group in which an aromatic ring is fused to one or more cycloalkyl rings. Non-limiting examples of the aryl group include a phenyl group, a naphthyl group, and a tetrahydronaphthyl group. At least one hydrogen atom in the aryl group may be substituted with the same substituent as in the case of the above-described alkyl group.

An arylalkyl group refers to an alkyl group-aryl group-, in which case the alkyl group and the aryl group are as described above.

A heteroaryl group refers to a monocyclic or bicyclic organic compound in which one or more heteroatoms N, O, P, or S are included and the remaining ring atom is carbon. The heteroaryl group may include 1 to 5 heteroatoms, and may include 5 to 10 ring members. The S or N may be oxidized to have various oxidation states. Examples of the monocyclic heteroaryl group may include a thienyl group, a furyl group, a pyrrolyl group, an imidazolyl group, a pyrazolyl group, a thiazolyl group, an isothiazolyl group, a 1,2,3-oxadiazolyl group, a 1,2,4-oxadiazolyl group, a 1,2,5-oxadiazolyl group, a 1,3,4-oxadiazolyl group, a 1,2,3-thiadiazolyl group, a 1,2,4-thiadiazolyl group, a 1,2,5-thiadiazolyl group, a 1,3,4-thiadiazolyl group, an isothiazol-3-yl group, an isothiazol-4-yl group, and isothiazol-5-yl group, and oxazol-2-yl group, an oxazol-4-yl group, an oxazol-5-yl group, an isoxazol-3-yl group, an isoxazol-4-yl group, an isoxazol-5-yl group, a 1,2,4-triazol-3-yl group, a 1,2,4-triazol-5-yl group, a 1,2,3-triazol-4-yl group, a 1,2,3-triazol-5-yl group, a tetrazolyl group, a pyrid-2-yl group, a pyrid-3-yl group, a 2-pyrazin-2-yl group, a pyrazin-4-yl group, a pyrazin-5-yl group, a 2-pyrimidin-2-yl group, a 4-pyrimidin-2-yl group, and a 5-pyrimidin-2-yl. Heteroaryl includes a case where a heteroaromatic ring is fused to one or more aryl, cycloaliphatic, or heterocycles. Examples of bicyclic heteroaryl include indolyl, isoindolyl, indazolyl, indolizinyl, purinyl, quinolizinyl, quinolinyl, and isoquinolinyl. At least one hydrogen atom in such heteroaryl may be substituted with the same substituent as in the case of the above-described alkyl group.

A heteroarylalkyl group refers to an alkyl group-heteroaryl group, in which case the heteroaryl group and the alkyl group are as described above. A heteroaryloxy group refers to a heteroaryl group —O—, in which case the heteroaryl group is as described above.

The term "room temperature" used herein refers to a temperature of about 25° C.

Hereinafter, the present disclosure will be described with reference to Examples and Comparative Examples below. However, the following examples are only examples of the present disclosure, and the present disclosure is not limited to these examples.

EXAMPLES

Synthesis of Photoacid Generator

Synthesis Example 1: Synthesis of PAG A

A compound (PAG A) was synthesized according to Reaction Formula A.

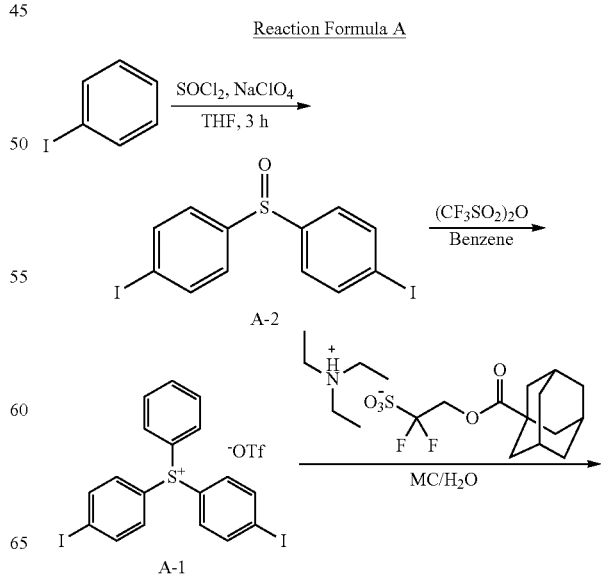

23

-continued

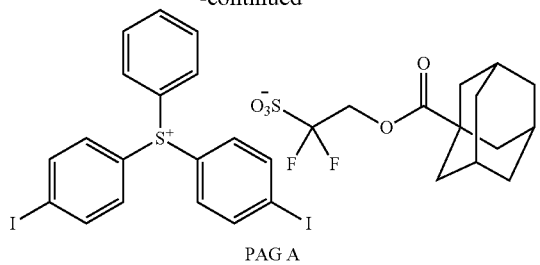

PAG A

Synthesis of Compound A-2

Iodobenzene (2.246 grams (g), 11.01 millimole (mmol)), thionyl chloride (0.655 g, 5.51 mmol), and sodium perchlorate (0.117 g, 1.10 mmol) were mixed with 12 milliliter (mL) of tetrahydrofuran and then stirred for 3 hours. Subsequently, after the reaction solvent was removed by reduced-pressure distillation, an organic layer obtained by extraction with 30 mL of water and 30 mL of methylene chloride was dried by anhydrous $Na_2SO_4$ and filtered. The residue obtained by processing the resulting filtrate under reduced pressure was separated and purified by silica gel chromatography to obtain compound A-2 (3.75 g, 75%). The obtained compound was analyzed by NMR and LC-MS.

$^1$H NMR (300 MHz, $CDCl_3$): δ 7.05 (d, 4H), 7.42 (d, 4H), LC-MS m/z=454.85 (M+H).

Synthesis of Compound A-1

After the compound A-2 (3.73 g, 8.20 mmol) was dissolved in 15 mL of benzene, trifluoromethanesulfonic anhydride (2.778 g, 9.85 mmol) was added dropwise at 0° C., followed by stirring at room temperature for 1 hour. Subsequently, an organic layer obtained by extraction with 20 mL of water and 50 mL of ethyl acetate was washed with a saturated aqueous $NaHCO_3$ solution, dried by anhydrous $Na_2SO_4$, and filtered. The residue obtained by processing the resulting filtrate under reduced pressure was separated and purified by silica gel chromatography to obtain compound A-1 (4.92 g, 90%). The obtained compound was analyzed by NMR and LC-MS.

$^1$H NMR (300 MHz, $CD_2Cl_2$): δ 8.08 (d, 4H), 7.84 (t, 1H), 7.74 (t, 2H), 7.69 (d, 2H), 7.41 (d, 2H), LC-MS m/z=514.88 (Cation)

Synthesis of Compound PAG A

The compound A-1 (4.91 g, 7.39 mmol) and triethylammonium 2-(1-adamantanecarbonyloxy)-1,1-difluoroethanesulfonate (3.146 g, 7.39 mmol) was mixed with 45 mL of methylene chloride and 5 mL of water and then stirred for 1 hour. Subsequently, an organic layer was separated, dried with anhydrous $MgSO_4$, and filtered. Then, the residue obtained by processing the resulting filtrate under reduced pressure was separated and purified by silica gel chromatography to obtain compound PAG A (5.7 g, yield 90%, purity 99%). The obtained compound was analyzed by NMR and MALDI.

$^1$H NMR (300 MHz, $CD_2Cl_2$): δ 8.08 (d, 4H), 7.84 (t, 1H), 7.74 (t, 2H), 7.69 (d, 2H), 7.41 (d, 4H), 4.63 (t, 2H), 2.00 (m, 3H), 1.89 (m, 6H), 1.71 (m, 3H), HRMS(MALDI) calcd for $C_{31}H_{30}F_2I_2O_5S_2$: m/z 837.96 Found: 837.95

24

Synthesis Example 2: Synthesis of PAG B

A compound (PAG B) was synthesized according to Reaction Formula B.

Reaction Formula B

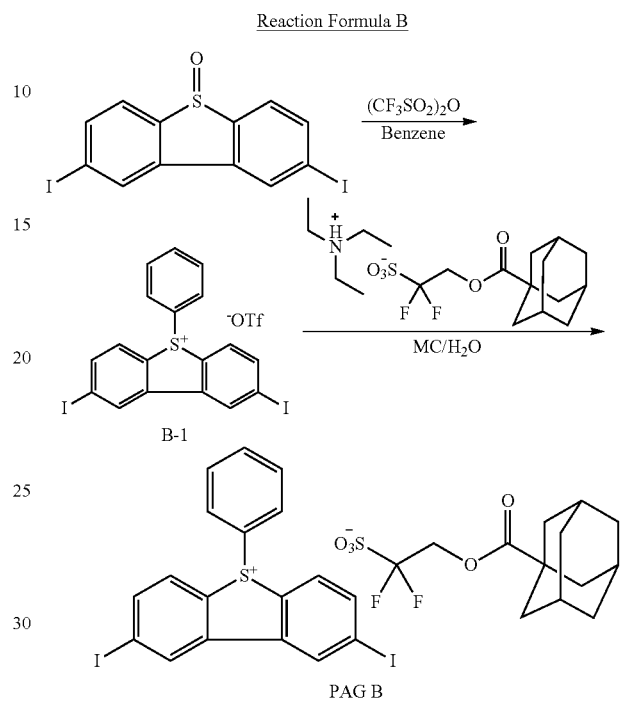

PAG B

Synthesis of Compound B-1

Compound B-1 (yield of 88%) was obtained in the same manner as the synthesis method of the compound A-1 in Synthesis Example 1, except that 2,8-diiododibenzothiophene 5-oxide was used instead of the compound A-2. The obtained compound was analyzed by NMR and LC-MS.

$^1$H NMR (300 MHz, $CD_2Cl_2$): δ 8.51 (s, 2H), 8.05 (d, 2H), 7.91 (d, 2H), 7.72 (t, 1H), 7.65 (d, 2H), 7.58 (t, 2H), LC-MS m/z=512.87 (Cation)

Synthesis of Compound PAG B

Compound PAG B (yield of 78%, purity of 99%) was obtained in the same manner as the synthesis method of the compound PAG A in Synthesis Example 1, except that the compound B-1 was used instead of the compound A-1. The obtained compound was analyzed by NMR and MALDI.

$^1$H NMR (300 MHz, $CD_2Cl_2$): δ 8.51 (s, 2H), 8.05 (d, 2H), 7.91 (d, 2H), 7.72 (t, 1H), 7.65 (d, 2H), 7.58 (t, 2H), 4.63 (t, 2H), 2.00 (m, 3H), 1.89 (m, 6H), 1.71 (m, 3H), HRMS(MALDI) calcd for $C_{31}H_{28}F_2I_2O_5S_2$: m/z 835.94 Found: 835.94

Synthesis Example 3: Synthesis of PAG C

A compound (PAG C) was synthesized according to Reaction Formula C.

Reaction Formula C

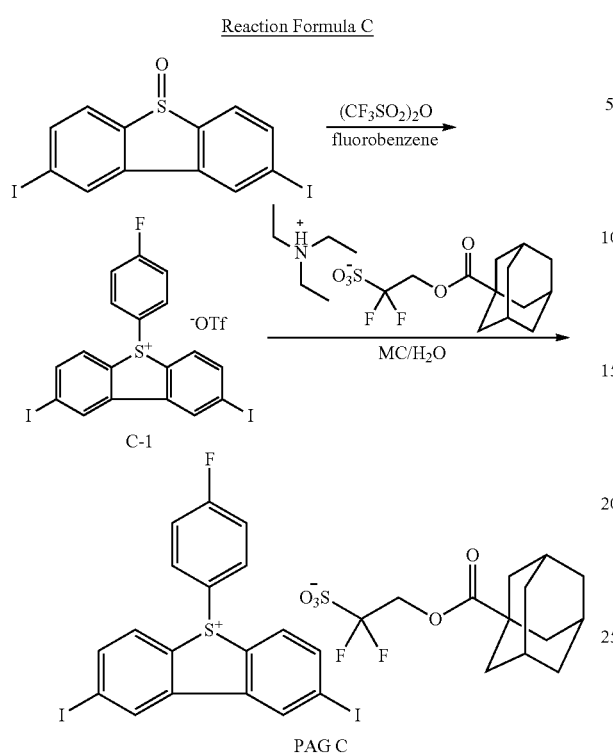

PAG C

Synthesis of Compound C-1

Compound C-1 (yield of 81%) was obtained in the same manner as the synthesis method of the compound B-1 in Synthesis Example 2, except that fluorobenzene was used instead benzene. The obtained compound was analyzed by NMR and LC-MS.

$^1$H NMR (300 MHz, CD$_2$Cl$_2$): δ 8.50 (s, 2H), 8.05 (d, 2H), 7.96 (d, 2H), 7.74 (m, 2H), 7.26 (m, 2H), LC-MS m/z=530.86 (Cation)

Synthesis of Compound PAG C

Compound PAG C (yield of 76%, purity of 99%) was obtained in the same manner as the synthesis method of the compound PAG A in Synthesis Example 1, except that the compound C-1 was used instead of the compound A-1. The obtained compound was analyzed by NMR and MALDI.

$^1$H NMR (300 MHz, CD$_2$Cl$_2$): δ 8.50 (s, 2H), 8.05 (d, 2H), 7.96 (d, 2H), 7.74 (m, 2H), 7.26 (m, 2H), 4.63 (t, 2H), 2.00 (m, 3H), 1.89 (m, 6H), 1.71 (m, 3H), HRMS(MALDI) calcd for C$_{31}$H$_{27}$F$_3$I$_2$O$_5$S$_2$: m/z 853.93 Found: 853.93

Synthesis Example 4: Synthesis of PAG D

A compound (PAG D) was synthesized according to Reaction Formula D.

Reaction Formula D

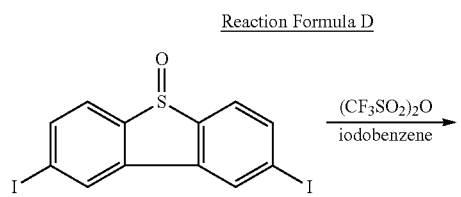

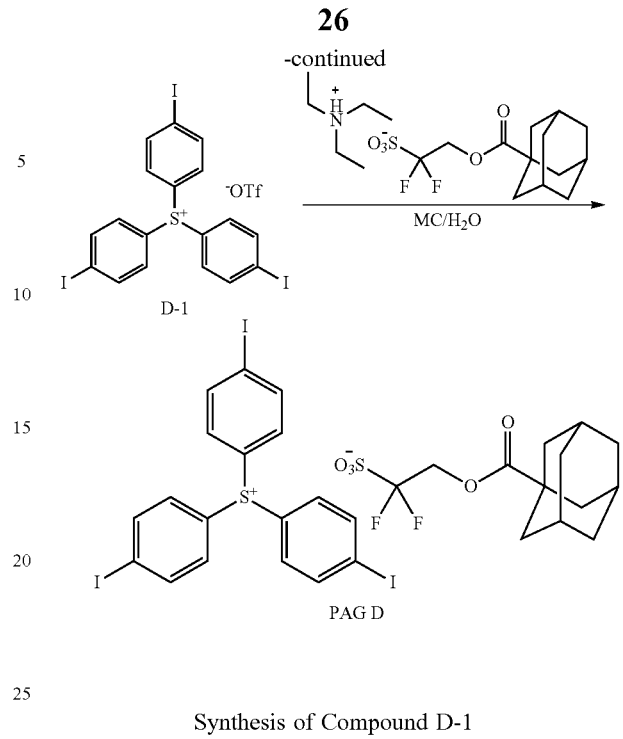

PAG D

Synthesis of Compound D-1

Compound D-1 (yield of 73%) was obtained in the same manner as the synthesis method of the compound A-1 in Synthesis Example 1, except that iodobenzene was used instead benzene. The obtained compound was analyzed by NMR and LC-MS.

$^1$H NMR (300 MHz, CD$_2$Cl$_2$): 8.08 (d, 6H), 7.41 (d, 6H), LC-MS m/z=640.78 (Cation)

Synthesis of Compound PAG D

Compound PAG D (yield of 67%, purity of 99%) was obtained in the same manner as the synthesis method of the compound PAG A in Synthesis Example 1, except that the compound D-1 was used instead of the compound A-1. The obtained compound was analyzed by NMR and MALDI.

$^1$H NMR (300 MHz, CD$_2$Cl$_2$): δ 8.08 (d, 6H), 7.41 (d, 6H), 4.63 (t, 2H), 2.00 (m, 3H), 1.89 (m, 6H), 1.71 (m, 3H), HRMS(MALDI) calcd for C$_{31}$H$_{29}$F$_2$I$_3$O$_5$S$_2$: m/z 963.86 Found: 963.85

Synthesis Example 5: Synthesis of PAG E

A compound (PAG E) was synthesized according to Reaction Formula E.

Reaction Formula E

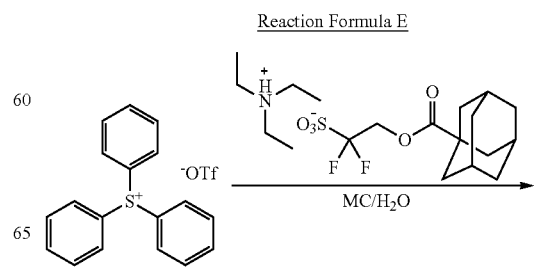

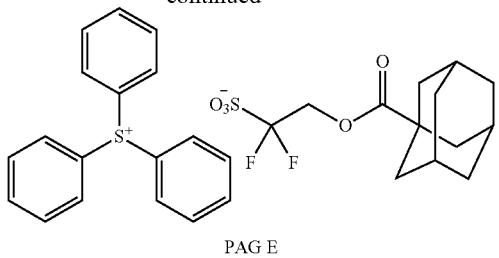

PAG E

Compound PAG E (yield of 93%, purity of 99%) was obtained in the same manner as the synthesis method of the compound PAG A in Synthesis Example 1, except that triphenylsulfonium triflate was used instead of the compound A-1. The obtained compound was analyzed by NMR and MALDI.

$^{1}$H NMR (300 MHz, CD$_2$Cl$_2$): δ 7.85 (m, 15H), 4.52 (t, 2H), 1.98 (m, 3H), 1.83 (m, 6H), 1.67 (m, 3H), HRMS (MALDI) calcd for C$_{31}$H$_{32}$F$_2$O$_5$S$_2$: m/z 586.17 Found: 586.16

Synthesis Example 6: Synthesis of PAG F

A compound (PAG F) was synthesized according to Reaction Formula F.

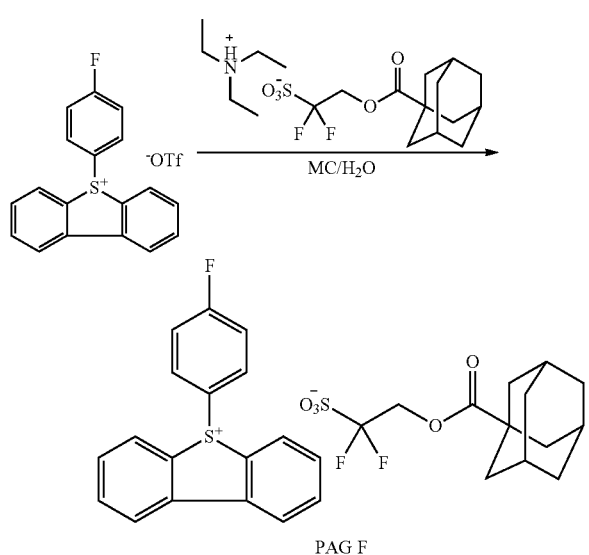

PAG F

Compound PAG F (yield of 93%, purity of 99%) was obtained in the same manner as the synthesis method of the compound PAG A in Synthesis Example 1, except that 5-(4-fluorophenyl)-5H-dibenzo[b,d]thiophen-5-ium triflate was used instead of the compound A-1. The obtained compound was analyzed by NMR and MALDI.

$^{1}$H NMR (300 MHz, CD$_2$Cl$_2$): δ 8.20 (m, 4H), 7.90 (t, 2H), 7.75 (m, 2H), 7.00 (t, 2H), 7.25 (t, 2H), 4.68 (t, 2H), 2.02 (m, 3H), 1.90 (m, 6H), 1.71 (m, 3H), HRMS(MALDI) calcd for C$_{31}$H$_{29}$F$_3$O$_5$S$_2$: m/z 602.14 Found: 602.13

Synthesis Example 7: Synthesis of PAG G

A compound (PAG G) was synthesized according to Reaction Formula G.

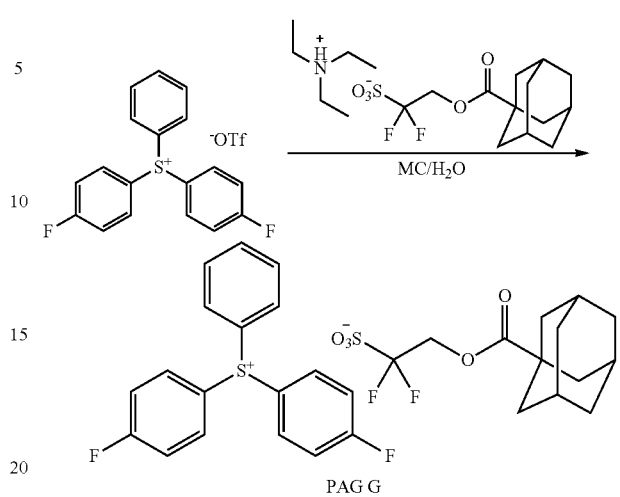

PAG G

Compound PAG G (yield of 93%, purity of 99%) was obtained in the same manner as the synthesis method of the compound PAG A in Synthesis Example 1, except that bis(4-fluorophenyl)(phenyl)sulfonium triflate was used instead of the compound A-1. The obtained compound was analyzed by NMR and MALDI.

$^{1}$H NMR (300 MHz, CD$_2$Cl$_2$): δ 7.82 (m, 5H), 7.72 (m, 4H), 7.45 (t, 4H), 4.52 (t, 2H), 1.98 (m, 3H), 1.83 (m, 6H), 1.67 (m, 3H), HRMS(MALDI) calcd for C$_{31}$H$_{30}$F$_4$O$_5$S$_2$: m/z 622.15 Found: 622.14

Synthesis Example 8: Synthesis of PAG H

A compound (PAG H) was synthesized according to Reaction Formula H.

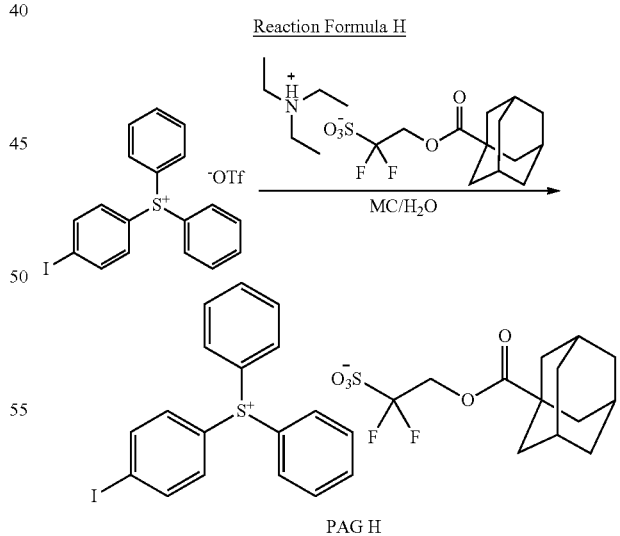

PAG H

Compound PAG H (yield of 87%, purity of 99%) was obtained in the same manner as the synthesis method of the compound PAG A in Synthesis Example 1, except that (4-iodophenyl)diphenylsulfonium triflate was used instead of the compound A-1. The obtained compound was analyzed by NMR and MALDI.

$^1$H NMR (300 MHz, CD$_2$Cl$_2$): 8.08 (d, 2H), 7.75 (m, 10H), 7.41 (d, 2H), 4.52 (t, 2H), 1.98 (m, 3H), 1.83 (m, 6H), 1.67 (m, 3H), HRMS(MALDI) calcd for C$_{31}$H$_{32}$F$_2$IO$_5$S$_2$: m/z 712.06 Found: 712.05

Synthesis of Base Polymer

Synthesis Example 9: Synthesis of Base Polymer

A base polymer represented by Formula 7-1 below was synthesized in the following manner.

0.94 g of dimethyl 2, 2'-azobis (2-methylpropionate) (manufactured by Waco Chemicals), 3.03 g of 2-ethyl-2-adamantylmethacrylate (manufactured by TCI Chemicals), and 1.98 g of 4-acetoxystyrene (manufactured by Sigma-Aldrich) were dissolved in tetrahydrofuran, and then polymerized at 80° C. for 8 hours. Then, the resulting product was precipitated using a methanol solvent, and then dried in a vacuum oven at 40° C. for 12 hours to obtain a polymer as a white powder. The obtained polymer was stirred in a mixed solution of sodium methoxide and methanol for 6 hours using a magnetic stir bar, and then acidified by acetic acid. Then, a precipitate obtained by precipitating the acidified polymer in distilled water was dried in a vacuum oven for 48 hours to obtain a polymer as a white powder represented by Formula 7-1 below.

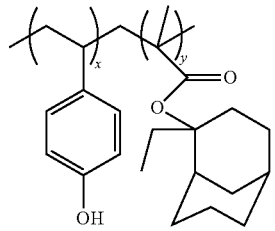

Formula 7-1 wherein in Formula 7-1, x and y are each 50.

Preparation of Photoresist Composition

Example 1: Preparation of Photoresist Composition 100 parts by weight of the base polymer prepared in Synthesis Example 9, 20.29 parts by weight the photoacid generator (PAG A) prepared in Synthesis Example 1, 12 parts by weight of the photodegradable quencher (Chemieliva Pharmaceutical Product List) represented by Formula 8, and 7500 parts by weight of a co-solvent obtained by mixing propylene glycol monoethyl ether acetate (Aldrich) and propylene glycol monomethyl ether (Aldrich) at a weight ratio of 30:70 was introduced into a reactor and mixed to prepare a photoresist composition.

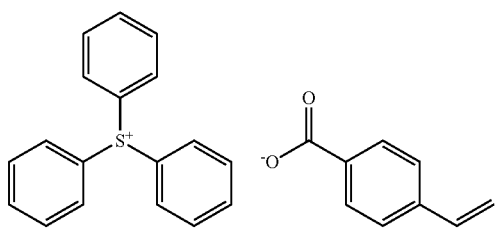

Formula 8

Example 2: Preparation of Photoresist Composition

A photoresist composition was prepared in the same manner as in Example 1, except that 26.25 parts by weight of the photoacid generator (PAG A) prepared in Synthesis Example 1 was used.

Example 3: Preparation of Photoresist Composition

A photoresist composition was prepared in the same manner as in Example 1, except that 37.73 parts by weight of the photoacid generator (PAG A) prepared in Synthesis Example 1 was used.

Example 4: Preparation of Photoresist Composition

A photoresist composition was prepared in the same manner as in Example 1, except that 20.24 parts by weight of the photoacid generator (PAG B) prepared in Synthesis Example 2 was used.

Example 5: Preparation of Photoresist Composition

A photoresist composition was prepared in the same manner as in Example 1, except that 26.18 parts by weight of the photoacid generator (PAG B) prepared in Synthesis Example 2 was used.

Example 6: Preparation of Photoresist Composition

A photoresist composition was prepared in the same manner as in Example 1, except that 37.64 parts by weight of the photoacid generator (PAG B) prepared in Synthesis Example 2 was used.

Example 7: Preparation of Photoresist Composition

A photoresist composition was prepared in the same manner as in Example 1, except that 20.68 parts by weight of the photoacid generator (PAG C) prepared in Synthesis Example 3 was used.

Example 8: Preparation of Photoresist Composition

A photoresist composition was prepared in the same manner as in Example 1, except that 26.74 parts by weight of the photoacid generator (PAG C) prepared in Synthesis Example 3 was used.

Example 9: Preparation of Photoresist Composition

A photoresist composition was prepared in the same manner as in Example 1, except that 38.45 parts by weight of the photoacid generator (PAG C) prepared in Synthesis Example 3 was used.

Example 10: Preparation of Photoresist Composition

A photoresist composition was prepared in the same manner as in Example 1, except that 23.34 parts by weight of the photoacid generator (PAG D) prepared in Synthesis Example 4 was used.

Example 11: Preparation of Photoresist Composition

A photoresist composition was prepared in the same manner as in Example 1, except that 30.19 parts by weight of the photoacid generator (PAG D) prepared in Synthesis Example 4 was used.

Example 12: Preparation of Photoresist Composition

A photoresist composition was prepared in the same manner as in Example 1, except that 43.40 parts by weight of the photoacid generator (PAG D) prepared in Synthesis Example 4 was used.

Comparative Example 1: Preparation of Photoresist Composition

A photoresist composition was prepared in the same manner as in Example 1, except that 14.20 parts by weight of the photoacid generator (PAG E) prepared in Synthesis Example 5 was used.

Comparative Example 2: Preparation of Photoresist Composition

A photoresist composition was prepared in the same manner as in Example 1, except that 18.36 parts by weight of the photoacid generator (PAG E) prepared in Synthesis Example 5 was used.

Comparative Example 3: Preparation of Photoresist Composition

A photoresist composition was prepared in the same manner as in Example 1, except that 26.40 parts by weight of the photoacid generator (PAG E) prepared in Synthesis Example 5 was used.

Comparative Example 4: Preparation of Photoresist Composition

A photoresist composition was prepared in the same manner as in Example 1, except that 14.58 parts by weight of the photoacid generator (PAG F) prepared in Synthesis Example 6 was used.

Comparative Example 5: Preparation of Photoresist Composition

A photoresist composition was prepared in the same manner as in Example 1, except that 18.86 parts by weight of the photoacid generator (PAG F) prepared in Synthesis Example 6 was used.

Comparative Example 6: Preparation of Photoresist Composition

A photoresist composition was prepared in the same manner as in Example 1, except that 27.12 parts by weight of the photoacid generator (PAG F) prepared in Synthesis Example 6 was used.

Comparative Example 7: Preparation of Photoresist Composition

A photoresist composition was prepared in the same manner as in Example 1, except that 15.07 parts by weight of the photoacid generator (PAG G) prepared in Synthesis Example 7 was used.

Comparative Example 8: Preparation of Photoresist Composition

A photoresist composition was prepared in the same manner as in Example 1, except that 19.49 parts by weight of the photoacid generator (PAG G) prepared in Synthesis Example 7 was used.

Comparative Example 9: Preparation of Photoresist Composition

A photoresist composition was prepared in the same manner as in Example 1, except that 28.02 parts by weight of the photoacid generator (PAG G) prepared in Synthesis Example 7 was used.

Comparative Example 10: Preparation of Photoresist Composition

A photoresist composition was prepared in the same manner as in Example 1, except that 17.24 parts by weight of the photoacid generator (PAG H) prepared in Synthesis Example 8 was used.

Comparative Example 11: Preparation of Photoresist Composition

A photoresist composition was prepared in the same manner as in Example 1, except that 22.30 parts by weight of the photoacid generator (PAG H) prepared in Synthesis Example 8 was used.

Comparative Example 12: Preparation of Photoresist Composition

A photoresist composition was prepared in the same manner as in Example 1, except that 32.07 parts by weight of the photoacid generator (PAG H) prepared in Synthesis Example 8 was used.

The composition of the photoresist compositions prepared according to Examples 1 to 12 and Comparative Examples 1 to 12 is summarized in Table 1 below.

TABLE 1

|  | Base polymer (parts by weight) | Photoacid generator (compound/parts by weight) | Photodegradable quencher (parts by weight) | Solvent (parts by weight) |
| --- | --- | --- | --- | --- |
| Example 1 | 100 | PAG A/20.29 | 12 | 7500 |
| Example 2 | 100 | PAG A/26.25 | 12 | 7500 |
| Example 3 | 100 | PAG A/37.73 | 12 | 7500 |
| Example 4 | 100 | PAG B/20.24 | 12 | 7500 |

TABLE 1-continued

| | Base polymer (parts by weight) | Photoacid generator (compound/parts by weight) | Photodegradable quencher (parts by weight) | Solvent (parts by weight) |
|---|---|---|---|---|
| Example 5 | 100 | PAG B/26.18 | 12 | 7500 |
| Example 6 | 100 | PAG B/37.64 | 12 | 7500 |
| Example 7 | 100 | PAG C/20.68 | 12 | 7500 |
| Example 8 | 100 | PAG C/26.74 | 12 | 7500 |
| Example 9 | 100 | PAG C/38.45 | 12 | 7500 |
| Example 10 | 100 | PAG D/23.34 | 12 | 7500 |
| Example 11 | 100 | PAGD/30.19 | 12 | 7500 |
| Example 12 | 100 | PAG D/43.40 | 12 | 7500 |
| Comparative Example 1 | 100 | PAG E/14.20 | 12 | 7500 |
| Comparative Example 2 | 100 | PAG E/18.36 | 12 | 7500 |
| Comparative Example 3 | 100 | PAG E/26.40 | 12 | 7500 |
| Comparative Example 4 | 100 | PAG F/14.58 | 12 | 7500 |
| Comparative Example 5 | 100 | PAG F/18.86 | 12 | 7500 |
| Comparative Example 6 | 100 | PAG F/27.12 | 12 | 7500 |
| Comparative Example 7 | 100 | PAG G/15.07 | 12 | 7500 |
| Comparative Example 8 | 100 | PAG G/19.49 | 12 | 7500 |
| Comparative Example 9 | 100 | PAG G/28.02 | 12 | 7500 |
| Comparative Example 10 | 100 | PAG H/17.24 | 12 | 7500 |
| Comparative Example 11 | 100 | PAG H/22.30 | 12 | 7500 |
| Comparative Example 12 | 100 | PAG H/32.07 | 12 | 7500 |

Evaluation Example 1: Evaluation of Photoresist Performance

A 12 inch circular silicon wafer substrate was pretreated for 10 minutes under a UV ozone cleaning system. Thereafter, the photoresist compositions prepared according to Examples 1 to 12 and Comparative Examples 1 to 12 were applied onto the pretreated wafer substrate at 1500 rpm for 30 seconds by spin coating, and were baked on a hot plate at 110° C. for 60 seconds (baked after application, post-apply bake, PAB) to form photoresist films each having a thickness of about 100 nm. EUV light (ASML NXE-3350) was radiated onto the wafer substrate coated with the photoresist film using a mask having a C/H pattern of a CD size of 25 nm and a pitch of 54 nm. Thereafter, the wafer substrate coated with the photoresist film was exposed on a hot plate at 90° C. for 60 seconds and then baked (post-exposure bake, PEB). The baked photoresist film was immersed in a 2.38% TMAH developer for 60 seconds. Thereafter, the resulting photoresist film was washed with deionized (DI) water for 10 seconds to remove and dry the coated portion not exposed to the EUV light, thereby forming photoresist patterns. The $E_{op}$, resolution, LER, and sensitivity of each of the photoresist patterns were measured using a CD-SEM (Critical Dimension Measurement Scanning Electron Microscope; measuring SEM). The measured values were substituted into Equation 1 below to obtain a Z-factor. The results thereof are shown in Table 2 and FIGS. 1 and 2.

$$Z\text{-factor}=(\text{resolution})^3 \times (\text{LER})^2 \times (\text{sensitivity}) \quad \text{Equation 1}$$

wherein in Equation 1, resolution is a CD size (half pitch, nm),

LER is CD uniformity (3σ of CD, nm), and

Sensitivity is $E_{op}$ (dose, millijoules per square centimeter (mJ/cm$^2$)).

TABLE 2

| | $E_{op}$ (mJ/cm$^2$) | LER (nm) | Z-factor |
|---|---|---|---|
| Example 1 | 43.7 | 1.60 | 8.95E−09 |
| Example 2 | 37.5 | 1.80 | 9.72E−09 |
| Example 3 | 32.3 | 2.00 | 1.03E−08 |
| Example 4 | 46.9 | 1.44 | 7.78E−09 |
| Example 5 | 38.3 | 1.70 | 8.85E−09 |
| Example 6 | 31.0 | 2.00 | 9.92E−09 |
| Example 7 | 45.3 | 1.65 | 9.87E−09 |
| Example 8 | 39.2 | 1.80 | 1.02E−08 |
| Example 9 | 29.8 | 2.10 | 1.05E−08 |
| Example 10 | 52.0 | 1.40 | 8.15E−09 |
| Example 11 | 40.1 | 1.68 | 9.05E−09 |
| Example 12 | 33.2 | 1.92 | 9.79E−09 |
| Comparative Example 1 | 54.7 | 2.10 | 1.93E−08 |
| Comparative Example 2 | 49.8 | 2.30 | 2.11E−08 |
| Comparative Example 3 | 42.3 | 2.60 | 2.29E−08 |
| Comparative Example 4 | 45.9 | 2.20 | 1.78E−08 |
| Comparative Example 5 | 38.2 | 2.35 | 1.69E−08 |
| Comparative Example 6 | 29.3 | 2.80 | 1.84E−08 |
| Comparative Example 7 | 48.3 | 2.20 | 1.87E−08 |

TABLE 2-continued

| | $E_{op}$ (mJ/cm$^2$) | LER (nm) | Z-factor |
|---|---|---|---|
| Comparative Example 8 | 36.4 | 2.35 | 1.61E−08 |
| Comparative Example 9 | 26.5 | 2.80 | 1.66E−08 |
| Comparative Example 10 | 43.3 | 1.82 | 1.15E−08 |
| Comparative Example 11 | 36.8 | 2.15 | 1.36E−08 |
| Comparative Example 12 | 30.1 | 2.55 | 1.57E−08 |

Figure 2:
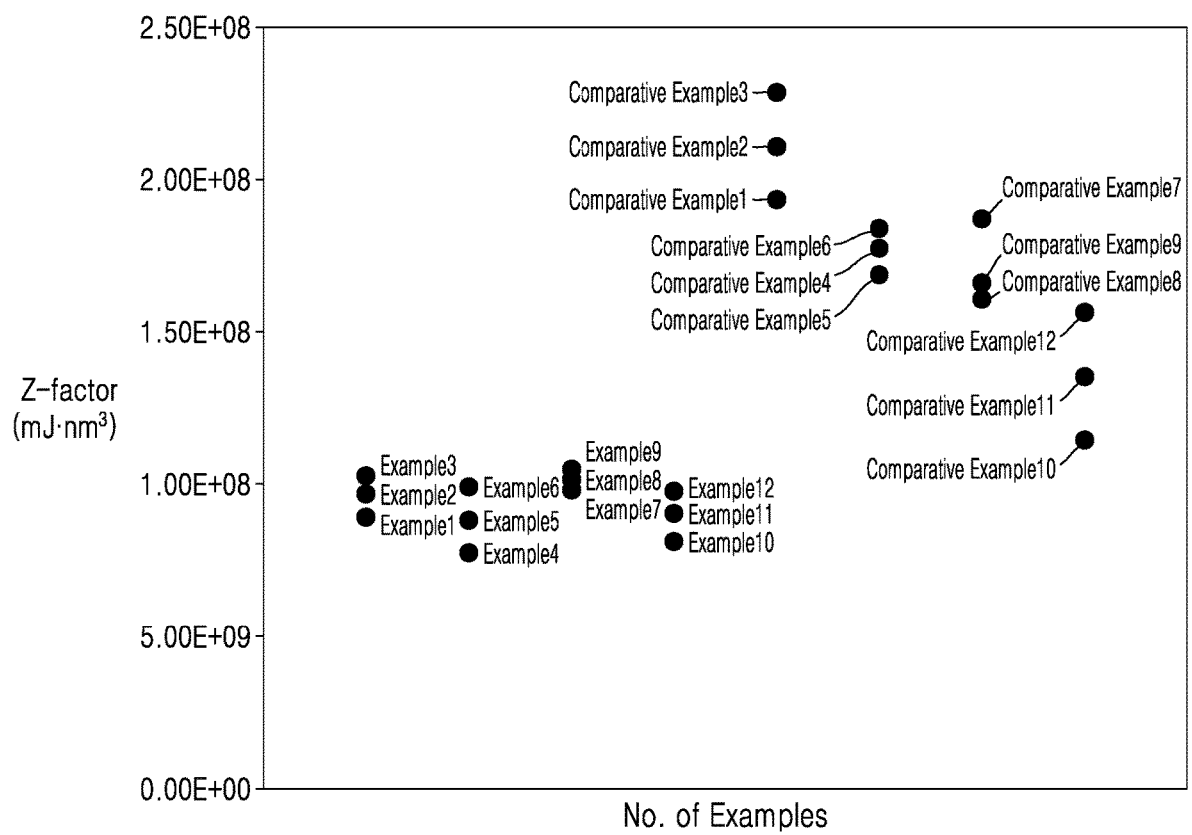
FIG. 2 is a graph illustrating Z-factor of photoresist patterns formed using the photoresist compositions of Examples 1 to 12 and Comparative Examples 1 to 12.

Referring to Table 2 and FIGS. 1 and 2, it may be found that, in the photoresist patterns using the photoresist films formed of the photoresist compositions prepared in Examples 1 to 12, LER and Z-factor with respect to $E_{op}$ are low, as compared with the photoresist patterns using the photoresist films formed of the photoresist compositions prepared in Comparative Examples 1 to 12.

Thus, it may be found that the photoresist compositions prepared in Examples 1 to 12 may provide improved lithography characteristics such as high sensitivity and high resolution and an improved pattern shape as compared with the photoresist compositions prepared in Comparative Examples 1 to 12.

The photoacid generator according to an aspect of an embodiment is provided with two or more iodine groups having a high light absorption rate as functional groups, thereby providing improved pattern resolution when forming a pattern using an EUV light source even with the same or less content as compared with the pattern formed using other light sources than the EUV light source.

The photoresist composition according to an aspect of an embodiment may provide improved lithography characteristics such as high sensitivity and high resolution and an improved pattern shape.

According to an aspect of an embodiment, the cation moiety of the photoacid generator is prepared through an electrophilic aromatic substitution reaction to obtain a photoacid generator having high purity.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the present detailed description as defined by the following claims.

What is claimed is:

1. A photoacid generator comprising a cation represented by Formula 3 and a counter anion,

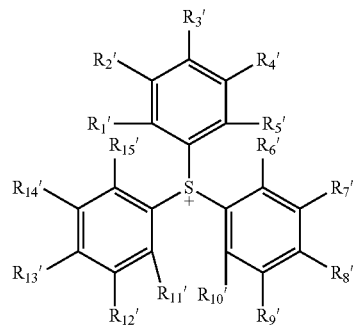

Formula 3 wherein, in Formula 3, $R_1'$, $R_2'$, $R_3'$, $R_4'$, and $R_5'$ are each independently a hydrogen atom, a halogen atom, a C1-C20 alkyl group, or a C1-C20 haloalkyl group, $R_6'$, $R_7'$, $R_8'$, $R_9'$, $R_{10}'$, $R_{11}'$, $R_{12}'$, $R_{13}'$, $R_{14}'$, and $R_{15}'$ are each independently a hydrogen atom, a halogen atom, a hydroxy group, a cyano group, a substituted or unsubstituted C1-C30 alkyl group, a substituted or unsubstituted C1-C30 alkoxy group, a substituted or unsubstituted C3-C30 cycloalkyl group, a substituted or unsubstituted C6-C30 aryl group, or a substituted or unsubstituted C6-C30 heteroaryl group, or $R_{10}'$ and $R_{11}'$ join to form a ring system, and at least two of $R_6'$, $R_7'$, $R_8'$, $R_9'$, $R_{12}'$, $R_{13}'$, $R_{14}'$, and $R_{15}'$ are iodine atoms.

2. The photoacid generator of claim 1, wherein $R_1'$, $R_2'$, $R_3'$, $R_4'$, and $R_5'$ are each independently hydrogen, fluorine, chlorine, bromine, a C1-C20 alkyl group, a C1-C20 alkyl fluoride group, a C1-C20 alkyl chloride group, or a C1-C20 alkyl bromide group.

3. The photoacid generator of claim 1, wherein the cation represented by Formula 3 comprises a cation represented by Formula 4 or Formula 5:

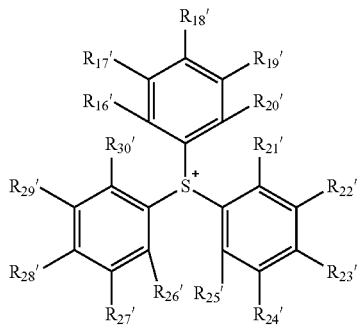

Formula 4 wherein, in Formula 4, $R_{16}'$, $R_{17}'$, $R_{18}'$, $R_{19}'$, and $R_{20}'$ are each independently a hydrogen atom, a halogen atom, a C1-C20 alkyl group, or a C1-C20 haloalkyl group, $R_{21}'$, $R_{22}'$, $R_{23}'$, $R_{24}'$, $R_{25}'$, $R_{26}'$, $R_{27}'$, $R_{28}'$, $R_{29}'$, and $R_{30}'$ are each independently a hydrogen atom, a halogen atom, a hydroxy group, a substituted or unsubstituted C1-C30 alkyl group, a substituted or unsubstituted C3-C30 cycloalkyl group, a substituted or unsubstituted C6-C30 aryl group, or a combination thereof, and at least two of $R_{23}'$, $R_{24}'$, $R_{27}'$, and $R_{28}'$ are iodine atoms,

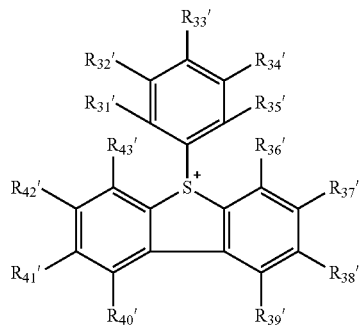

Formula 5 wherein, in Formula 5,
$R_{31}'$, $R_{32}'$, $R_{33}'$, $R_{34}'$, and $R_{35}'$ are each independently a hydrogen atom, a halogen atom, a C1-C20 alkyl group, or a C1-C20 haloalkyl group,
$R_{36}'$, $R_{37}'$, $R_{38}'$, $R_{39}'$, $R_{40}'$, $R_{41}'$, $R_{42}'$, and $R_{43}'$ are each independently a hydrogen atom, a halogen atom, a hydroxy group, a substituted or unsubstituted C1-C30 alkyl group, a substituted or unsubstituted C3-C30 cycloalkyl group, a substituted or unsubstituted C6-C30 aryl group, or a combination thereof, and at least two of $R_{38}'$, $R_{39}'$, $R_{40}'$, and $R_{41}'$ are iodine atoms.

4. The photoacid generator of claim 3, wherein $R_{16}'$, $R_{17}'$, $R_{18}'$, $R_{19}'$, $R_{20}'$, $R_{31}'$, $R_{32}'$, $R_{33}'$, $R_{34}'$, and $R_{35}'$ are each independently hydrogen, fluorine, chlorine, bromine, a C1-C20 alkyl group, a C1-C20 alkyl fluoride group, a C1-C20 alkyl chloride group, or a C1-C20 alkyl bromide group.

5. The photoacid generator of claim 1, wherein the counter anion includes an anion represented by Formula 6:

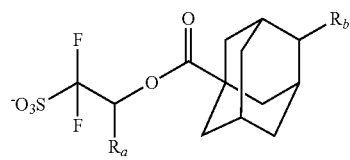

Formula 6 wherein, in Formula 6,
$R_a$ and $R_b$ are each independently a hydrogen atom, a halogen atom, a C1-C20 alkyl group, or a C1-C20 haloalkyl group.

6. A photoresist composition comprising:
the photoacid generator of claim 1;
a base polymer;
a photodegradable quencher (PDQ); and
a solvent.

7. The photoresist composition of claim 6, wherein the content of the photoacid generator is about 15 parts by weight to about 50 5 parts by weight based on 100 parts by weight of the base polymer.

8. The photoresist composition of claim 6, wherein the base polymer comprises a polymer represented by Formula 7:

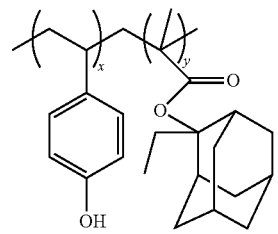

Formula 7 wherein, in Formula 7,
x is an integer of 1 to 100, and y is an integer of 1 to 100.

9. The photoresist composition of claim 6, wherein the photodegradable quencher comprises a quencher represented by Formula 8:

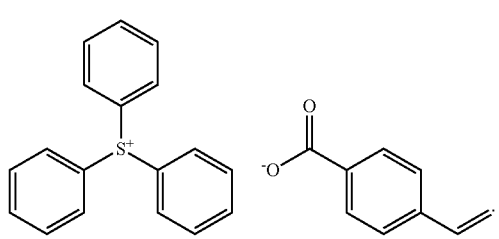

Formula 8

10. The photoresist composition of claim 6, wherein the solvent comprises polypropylene glycol monomethyl ether acetate, propylene glycol monomethyl ether, or a combination thereof.

11. The photoresist composition of claim 6, wherein, in the Formula 3 of the cation, $R_1'$, $R_2'$, $R_3'$, $R_4'$, and $R_5'$ are each independently hydrogen, fluorine, chlorine, bromine, a C1-C20 alkyl group, a C1-C20 alkyl fluoride group, a C1-C20 alkyl chloride group, or a C1-C20 alkyl bromide group.

12. The photoresist composition of claim 6, wherein the cation represented by Formula 3 comprises a cation represented by Formula 4 or Formula 5:

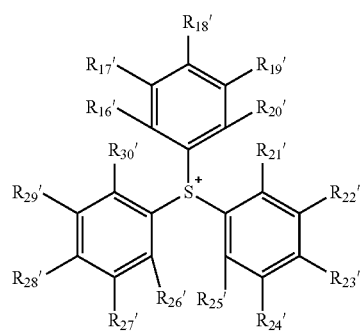

Formula 4 wherein, in Formula 4,
$R_{16}'$, $R_{17}'$, $R_{18}'$, $R_{19}'$, and $R_{20}'$ are each independently a hydrogen atom, a halogen atom, a C1-C20 alkyl group, or a C1-C20 haloalkyl group,
$R_{21}'$, $R_{22}'$, $R_{23}'$, $R_{24}'$, $R_{25}'$, $R_{26}'$, $R_{27}'$, $R_{28}'$, $R_{29}'$, and $R_{30}'$ are each independently a hydrogen atom, a halogen atom, a hydroxy group, a substituted or unsubstituted C1-C30 alkyl group, a substituted or unsubstituted C3-C30 cycloalkyl group, a substituted or unsubstituted C6-C30 aryl group, or a combination thereof, and at least two of $R_{23}'$, $R_{24}'$, $R_{27}'$, and $R_{28}'$ are iodine atoms, Formula 5

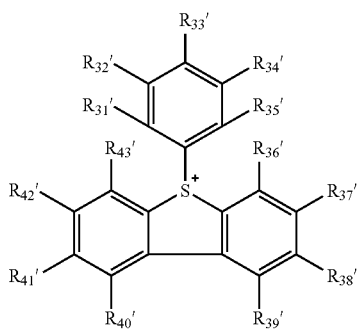

wherein, in Formula 5, $R_{31}'$, $R_{32}'$, $R_{33}'$, $R_{34}'$, and $R_{35}'$ are each independently a hydrogen atom, a halogen atom, a C1-C20 alkyl group, or a C1-C20 haloalkyl group, $R_{36}'$, $R_{37}'$, $R_{38}'$, $R_{39}'$, $R_{40}'$, $R_{41}'$, $R_{42}'$, and $R_{43}'$ are each independently a hydrogen atom, a halogen atom, a hydroxy group, a substituted or unsubstituted C1-C30 alkyl group, a substituted or unsubstituted C3-C30 cycloalkyl group, a substituted or unsubstituted C6-C30 aryl group, or a combination thereof, and at least two of $R_{38}'$, $R_{39}'$, $R_{40}'$, and $R_{41}'$ are iodine atoms.

13. The photoresist composition of claim 12, wherein $R_{16}'$, $R_{17}'$, $R_{18}'$, $R_{19}'$, $R_{20}'$, $R_{31}'$, $R_{32}'$, $R_{33}'$, $R_{34}'$, and $R_{35}'$ are each independently hydrogen, fluorine, chlorine, bromine, a C1-C20 alkyl group, a C1-C20 alkyl fluoride group, a C1-C20 alkyl chloride group, or a C1-C20 alkyl bromide group.

14. The photoresist composition of claim 6, wherein the counter anion includes an anion represented by Formula 6:

Formula 6

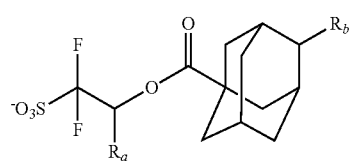

wherein, in Formula 6, $R_a$ and $R_b$ are each independently a hydrogen atom, a halogen atom, a C1-C20 alkyl group, or a C1-C20 haloalkyl group.

15. A pattern formation method comprising:
forming a photoresist film by applying the photoresist composition of claim 6 on a substrate;
exposing at least a portion of the photoresist film to high energy rays; and
developing an exposed photoresist film using a developing solution.

16. The pattern formation method of claim 15, wherein the exposing is performed by irradiating at least one of an ultraviolet (UV), a deep ultraviolet (DUV), an extreme ultraviolet (EUV), and an electron beam (EB) rays.

17. The pattern formation method of claim 15, wherein the base polymer of the photoresist composition comprises a polymer represented by Formula 7:

Formula 7

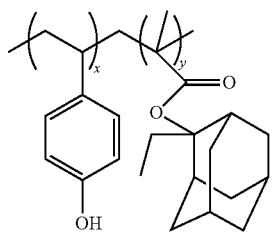

wherein, in Formula 7,
x is an integer of 1 to 100, and y is an integer of 1 to 100.

18. The pattern formation method of claim 15, wherein the cation represented by Formula 3 of the photoacid generator of the photoresist composition comprises a cation represented by Formula 4 or Formula 5:

Formula 4

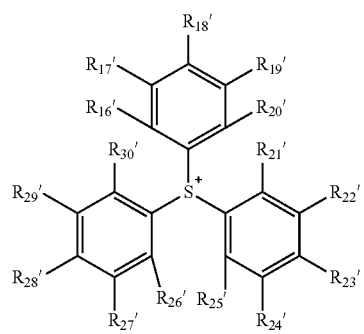

wherein, in Formula 4, $R_{16}'$, $R_{17}'$, $R_{18}'$, $R_{19}'$, and $R_{20}'$ are each independently a hydrogen atom, a halogen atom, a C1-C20 alkyl group, or a C1-C20 haloalkyl group, $R_{21}'$, $R_{22}'$, $R_{23}'$, $R_{24}'$, $R_{25}'$, $R_{26}'$, $R_{27}'$, $R_{28}'$, $R_{29}'$, and $R_{30}'$ are each independently a hydrogen atom, a halogen atom, a hydroxy group, a substituted or unsubstituted C1-C30 alkyl group, a substituted or unsubstituted C3-C30 cycloalkyl group, a substituted or unsubstituted C6-C30 aryl group, or a combination thereof, and at least two of $R_{23}'$, $R_{24}'$, $R_{27}'$, and $R_{28}'$ are iodine atoms, Formula 5

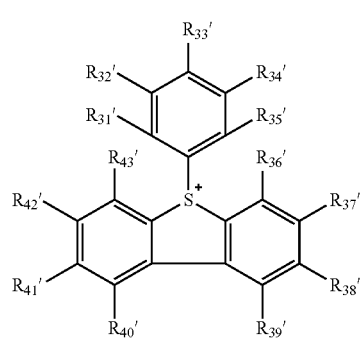

wherein, in Formula 5, $R_{31}'$, $R_{32}'$, $R_{33}'$, $R_{34}'$, and $R_{35}'$ are each independently a hydrogen atom, a halogen atom, a C1-C20 alkyl group, or a C1-C20 haloalkyl group, $R_{36}'$, $R_{37}'$, $R_{38}'$, $R_{39}'$, $R_{40}'$, $R_{41}'$, $R_{42}'$, and $R_{43}'$ are each independently a hydrogen atom, a halogen atom, a hydroxy group, a substituted or unsubstituted C1-C30 alkyl group, a substituted or unsubstituted C3-C30 cycloalkyl group, a substituted or unsubstituted C6-C30 aryl group, or a combination thereof, and at least two of $R_{38}'$, $R_{39}'$, $R_{40}'$, and $R_{41}'$ are iodine atoms.

19. The pattern formation method of claim 15, wherein the counter anion of the photoacid generator of the photoresist composition includes an anion represented by Formula 6:

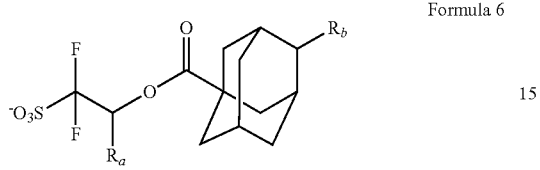

Formula 6 wherein, in Formula 6, $R_a$ and $R_b$ are each independently a hydrogen atom, a halogen atom, a C1-C20 alkyl group, or a C1-C20 haloalkyl group.

20. The photoresist composition of claim 6, wherein the content of the photoacid generator is about 15 parts by weight to about 45 parts by weight based on 100 parts by weight of the base polymer.

21. The photoresist composition of claim 6, wherein the content of the photoacid generator is about 15 parts by weight to about 40 parts by weight based on 100 parts by weight of the base polymer.

* * * * *